United States Patent
Edwards et al.

(10) Patent No.: US 7,678,364 B2
(45) Date of Patent: Mar. 16, 2010

(54) PARTICLES FOR INHALATION HAVING SUSTAINED RELEASE PROPERTIES

(75) Inventors: David A. Edwards, Boston, MA (US); Jeffrey S. Hrkach, Cambridge, MA (US)

(73) Assignee: Alkermes, Inc., Waltham, MA (US)

( * ) Notice: Subject to any disclaimer, the term of this patent is extended or adjusted under 35 U.S.C. 154(b) by 1680 days.

(21) Appl. No.: 09/822,716

(22) Filed: Mar. 30, 2001

(65) Prior Publication Data

US 2002/0034477 A1 Mar. 21, 2002

Related U.S. Application Data

(63) Continuation-in-part of application No. 09/383,054, filed on Aug. 25, 1999.

(51) Int. Cl.
*A61K 9/12* (2006.01)
*A61K 9/14* (2006.01)
*A61K 38/28* (2006.01)
*A61K 33/30* (2006.01)

(52) U.S. Cl. .................. 424/46; 424/459; 424/489; 424/499; 514/2; 514/3

(58) Field of Classification Search .................. 424/45, 424/46, 489, 426, 499, 501, 434; 514/2, 514/3, 4, 12, 13
See application file for complete search history.

(56) References Cited

U.S. PATENT DOCUMENTS

| | | | |
|---|---|---|---|
| 2,470,296 A | 5/1949 | Fields | |
| 2,533,065 A | 12/1950 | Taplin et al. | |
| 2,992,645 A | 7/1961 | Fowler | |
| 3,102,077 A * | 8/1963 | Christensen | 530/304 |
| 3,781,230 A | 12/1973 | Vassiliades et al. | |
| 3,957,965 A | 5/1976 | Harley et al. | |
| 4,009,280 A | 2/1977 | Macarthur et al. | |
| 4,069,819 A | 1/1978 | Valentini et al. | 128/206 |
| 4,089,800 A | 5/1978 | Temple | |
| 4,161,516 A | 7/1979 | Bell | |
| 4,173,488 A | 11/1979 | Vassiliades et al. | |
| 4,272,398 A | 6/1981 | Jaffe | |
| 4,352,883 A | 10/1982 | Lim | |
| 4,391,909 A | 7/1983 | Lim | |
| 4,459,226 A | 7/1984 | Grimes et al. | 260/112.7 |
| 4,466,442 A | 8/1984 | Hilmann et al. | |
| 4,480,041 A | 10/1984 | Myles et al. | |
| 4,524,769 A | 6/1985 | Wetterlin | |
| 4,572,203 A | 2/1986 | Feinstein | |
| 4,590,206 A | 5/1986 | Forrester et al. | |
| 4,615,697 A | 10/1986 | Robinson | |
| 4,679,555 A | 7/1987 | Sackner | |
| 4,741,872 A | 5/1988 | De Luca et al. | |
| 4,743,545 A | 5/1988 | Torobin | |
| 4,774,958 A | 10/1988 | Feinstein | |
| 4,789,550 A | 12/1988 | Hommel et al. | |
| 4,818,542 A | 4/1989 | De Luca et al. | |
| 4,847,091 A | 7/1989 | Illum | |
| 4,855,144 A | 8/1989 | Leong et al. | |
| 4,857,311 A | 8/1989 | Domb et al. | |
| 4,861,627 A | 8/1989 | Mathiowitz et al. | |
| 4,865,789 A | 9/1989 | Castro et al. | |
| 4,895,719 A | 1/1990 | Radhakrishnan et al. | 424/45 |
| 4,904,479 A | 2/1990 | Illum | |
| 4,917,119 A | 4/1990 | Potter et al. | |
| 4,963,297 A | 10/1990 | Madden | |
| 4,976,968 A | 12/1990 | Steiner | |
| 4,994,281 A | 2/1991 | Muranishi et al. | |
| 4,995,385 A | 2/1991 | Valentini et al. | 128/203.21 |
| 5,033,463 A | 7/1991 | Cocozza | |
| 5,064,650 A | 11/1991 | Lew | |

(Continued)

FOREIGN PATENT DOCUMENTS

CA 2085884 12/1991

(Continued)

OTHER PUBLICATIONS

International Cosmetic Ingredient Dictionary and Handbook, 7th edition, vol. 2, 1997, p. 1653.*

(Continued)

*Primary Examiner*—Mina Haghighatian
(74) *Attorney, Agent, or Firm*—Elmore Patent Law Group, PC; Carolyn S. Elmore; Darlene A. Vanstone

(57) ABSTRACT

The invention generally relates to a method for pulmonary delivery of therapeutic, prophylactic and diagnostic agents to a patient wherein the agent is released in a sustained fashion, and to particles suitable for use in the method. In particular, the invention relates to a method for the pulmonary delivery of a therapeutic, prophylactic or diagnostic agent comprising administering to the respiratory tract of a patient in need of treatment, prophylaxis or diagnosis an effective amount of particles comprising a multivalent metal cation which is complexed with a therapeutic, prophylactic or diagnostic agent or any combination thereof having a charge capable of complexing with the cation upon association with the agent, a pharmaceutically acceptable carrier and optionally, a multivalent metal cation-containing component wherein the total amount of multivalent metal cation present in the particles is more than 1% weight/weight of the total weight of the agent (% w/w). Release of the agent from the administered particles occurs in a sustained fashion.

30 Claims, 3 Drawing Sheets

U.S. PATENT DOCUMENTS

| | | | |
|---|---|---|---|
| 5,069,936 A | 12/1991 | Yen | |
| 5,070,186 A | 12/1991 | Joergensen | 530/304 |
| 5,075,109 A | 12/1991 | Tice et al. | |
| 5,100,669 A | 3/1992 | Hyon et al. | |
| 5,123,414 A | 6/1992 | Unger | |
| 5,145,684 A | 9/1992 | Liversidge et al. | |
| 5,160,745 A | 11/1992 | De Luca et al. | |
| 5,169,871 A | 12/1992 | Hughes et al. | |
| 5,174,988 A | 12/1992 | Mautone et al. | |
| 5,195,520 A | 3/1993 | Schlief et al. | |
| 5,204,108 A | 4/1993 | Illum | |
| 5,204,113 A | 4/1993 | Hartley et al. | |
| 5,260,306 A | 11/1993 | Boardman et al. | |
| 5,271,961 A | 12/1993 | Mathiowitz et al. | |
| 5,306,483 A | 4/1994 | Mautone | |
| 5,327,883 A | 7/1994 | Williams et al. | |
| 5,334,381 A | 8/1994 | Unger | |
| 5,340,587 A | 8/1994 | Milhalko et al. | |
| 5,352,435 A | 10/1994 | Unger | |
| 5,384,133 A | 1/1995 | Boyes et al. | |
| 5,393,524 A | 2/1995 | Quay | |
| 5,407,609 A | 4/1995 | Tice et al. | |
| 5,456,917 A | 10/1995 | Wise et al. | |
| 5,461,031 A | 10/1995 | DeFelippis | 514/4 |
| 5,466,841 A | 11/1995 | Horrobin et al. | |
| 5,474,978 A | 12/1995 | Bakaysa et al. | 514/4 |
| 5,482,946 A | 1/1996 | Clark et al. | |
| 5,504,188 A | 4/1996 | Baker et al. | 530/304 |
| 5,518,709 A | 5/1996 | Sutton et al. | |
| 5,518,998 A | 5/1996 | Bäckström et al. | |
| 5,534,488 A | 7/1996 | Hoffmann | 514/3 |
| 5,547,929 A | 8/1996 | Anderson, Jr. et al. | 514/3 |
| 5,551,489 A | 9/1996 | Trofast et al. | |
| 5,580,575 A | 12/1996 | Unger et al. | |
| 5,607,695 A | 3/1997 | Ek et al. | |
| 5,607,915 A | 3/1997 | Patton | |
| 5,612,053 A | 3/1997 | Baichwal et al. | |
| 5,614,216 A | 3/1997 | Janoff | |
| 5,654,007 A | 8/1997 | Johnson | |
| 5,690,954 A | 11/1997 | Illum | |
| 5,698,721 A | 12/1997 | Heath | |
| 5,707,644 A | 1/1998 | Illum | |
| 5,709,884 A | 1/1998 | Trofast et al. | |
| 5,780,014 A | 7/1998 | Eljamal | |
| 5,795,594 A | 8/1998 | York et al. | |
| 5,804,212 A | 9/1998 | Illum | |
| 5,814,607 A | 9/1998 | Patton | |
| 5,830,853 A | 11/1998 | Bäckström et al. | |
| 5,851,453 A | 12/1998 | Hanna et al. | |
| 5,855,913 A | 1/1999 | Hanes et al. | 424/489 |
| 5,874,063 A | 2/1999 | Briggner et al. | |
| 5,874,064 A | 2/1999 | Edwards et al. | 424/46 |
| 5,885,613 A | 3/1999 | Holland et al. | |
| 5,898,028 A | 4/1999 | Jensen et al. | |
| 5,902,802 A | 5/1999 | Heath | |
| 5,922,354 A | 7/1999 | Johnson | |
| 5,928,469 A | 7/1999 | Franks et al. | |
| 5,941,240 A | 8/1999 | Gonda et al. | 128/200.14 |
| 5,970,973 A | 10/1999 | Gonda et al. | 128/200.14 |
| 5,972,331 A | 10/1999 | Reichert et al. | 424/85.1 |
| 5,976,574 A | 11/1999 | Gordon | 424/489 |
| 5,985,248 A | 11/1999 | Gordon et al. | 424/46 |
| 5,985,309 A | 11/1999 | Edwards et al. | 424/426 |
| 5,993,783 A | 11/1999 | Eljamal | |
| 5,993,805 A | 11/1999 | Sutton et al. | 424/94.1 |
| 5,994,314 A | 11/1999 | Eljamal et al. | 514/44 |
| 5,997,848 A | 12/1999 | Patton et al. | 424/46 |
| 6,001,336 A | 12/1999 | Gordon | 424/46 |
| 6,019,968 A | 2/2000 | Platz | |
| 6,043,214 A * | 3/2000 | Jensen et al. | 514/3 |
| 6,045,828 A | 4/2000 | Bystrom et al. | 424/489 |
| 6,051,256 A | 4/2000 | Platz | |
| 6,063,138 A | 5/2000 | Hanna et al. | |
| 6,077,543 A | 6/2000 | Gordon et al. | 424/489 |
| 6,080,721 A | 6/2000 | Patton | |
| 6,080,762 A | 6/2000 | Allen et al. | 514/337 |
| 6,098,615 A | 8/2000 | Lloyd et al. | 128/200.14 |
| 6,103,270 A | 8/2000 | Johnson | |
| 6,123,936 A | 9/2000 | Platz | |
| 6,136,295 A | 10/2000 | Edwards et al. | 424/45 |
| 6,136,346 A | 10/2000 | Eljamal | |
| 6,153,224 A | 11/2000 | Staniforth | |
| RE37,053 E | 2/2001 | Hanes et al. | 424/489 |
| 6,187,330 B1 | 2/2001 | Wang et al. | |
| 6,187,344 B1 | 2/2001 | Eljamal | |
| 6,231,851 B1 | 5/2001 | Platz | |
| 6,254,854 B1 | 7/2001 | Edwards et al. | 424/46 |
| 6,258,341 B1 | 7/2001 | Foster | |
| 6,284,282 B1 * | 9/2001 | Maa et al. | 424/499 |
| 6,303,582 B1 | 10/2001 | Eljamal | |
| 6,309,623 B1 * | 10/2001 | Weers et al. | 424/45 |
| 6,309,671 B1 | 10/2001 | Foster | |
| 6,315,983 B1 | 11/2001 | Eistetter | |
| 6,358,530 B1 | 3/2002 | Eljamal | |
| 6,426,210 B1 | 7/2002 | Franks et al. | |
| 6,433,040 B1 | 8/2002 | Dellamary et al. | |
| 6,652,837 B1 * | 11/2003 | Edwards et al. | 424/45 |
| 6,749,835 B1 * | 6/2004 | Lipp et al. | 424/46 |
| 7,048,908 B2 * | 5/2006 | Basu et al. | 424/45 |
| 7,052,678 B2 * | 5/2006 | Vanbever et al. | 424/45 |
| 7,097,827 B2 * | 8/2006 | Platz et al. | 424/45 |
| 7,279,182 B2 * | 10/2007 | Lipp et al. | 424/489 |
| 2002/0052310 A1 | 5/2002 | Edwards et al. | |

FOREIGN PATENT DOCUMENTS

| | | |
|---|---|---|
| CA | 1300009 | 5/1992 |
| CA | 1302258 | 6/1992 |
| CA | 2166108 | 1/1995 |
| CA | 2170394 | 3/1995 |
| CA | 2244767 | 1/1997 |
| CA | 2111002 | 8/2000 |
| CA | 2058428 | 9/2000 |
| CA | 2126244 | 9/2000 |
| EP | 0 257 915 A1 | 3/1988 |
| EP | 0 317 120 A1 | 5/1989 |
| EP | 0 324 938 A1 | 7/1989 |
| EP | 0 335 133 A2 | 10/1989 |
| EP | 0 458 745 A1 | 5/1991 |
| EP | 0 213 303 B1 | 9/1991 |
| EP | 0 257 956 B1 | 5/1992 |
| EP | 0 510 731 A1 | 10/1992 |
| EP | 0 634 166 A1 | 1/1995 |
| EP | 0 655 237 A1 | 5/1995 |
| EP | 0 656 206 A1 | 6/1995 |
| EP | 0 072 046 A1 | 2/2003 |
| GB | 1 288 583 | 11/1969 |
| WO | WO 80/02365 | 11/1980 |
| WO | WO 86/06959 | 12/1986 |
| WO | WO 88/04556 | 6/1988 |
| WO | WO 88/09163 | 12/1988 |
| WO | WO 91/04732 | 4/1991 |
| WO | WO 91/06286 | 5/1991 |
| WO | WO 91/06287 | 5/1991 |
| WO | WO 91/12823 | 9/1991 |
| WO | WO 91/16882 | 11/1991 |
| WO | WO 92/18164 | 10/1992 |
| WO | WO 92/21382 | 12/1992 |
| WO | WO 93/25221 | 12/1993 |
| WO | WO 94/04133 | 3/1994 |
| WO | WO 94/07514 | 4/1994 |
| WO | WO 94/08627 | 4/1994 |
| WO | WO 94/16739 | 8/1994 |
| WO | WO 95/00127 | 1/1995 |

| | | |
|---|---|---|
| WO | WO 95/07072 | 3/1995 |
| WO | WO 95/24183 | 9/1995 |
| WO | WO 95/31479 | 11/1995 |
| WO | WO 95/35097 | 12/1995 |
| WO | WO 96/09814 | 4/1996 |
| WO | WO 96/15814 | 5/1996 |
| WO | WO 96/23485 | 8/1996 |
| WO | WO 96/32096 | 10/1996 |
| WO | WO 96/32116 | 10/1996 |
| WO | WO 96/32149 | 10/1996 |
| WO | WO 96/40963 | 12/1996 |
| WO | WO 96/41873 | 12/1996 |
| WO | WO 97/03649 | 6/1997 |
| WO | WO 97/26863 | 7/1997 |
| WO | WO 97/36574 | 10/1997 |
| WO | WO 97/41833 | 11/1997 |
| WO | WO 97/44012 | 11/1997 |
| WO | WO 98/16205 | 4/1998 |
| WO | WO 98/29096 | 7/1998 |
| WO | WO 98/29098 | 7/1998 |
| WO | WO 98/29140 | 7/1998 |
| WO | WO 98/29141 | 7/1998 |
| WO | WO 98/31346 | 7/1998 |
| WO | WO 98/51278 | 11/1998 |
| WO | WO 99/16419 | 4/1999 |
| WO | WO 99/16420 | 4/1999 |
| WO | WO 99/16421 | 4/1999 |
| WO | WO 99/16422 | 4/1999 |
| WO | WO 99/66903 | 12/1999 |
| WO | WO 02/09669 A3 | 2/2000 |
| WO | WO 00/10541 | 3/2000 |
| WO | WO 00/15262 | 3/2000 |
| WO | WO 00/21594 | 4/2000 |
| WO | WO 00/33811 | 6/2000 |
| WO | WO 01/00312 A1 | 1/2001 |
| WO | WO 01/13891 A3 | 3/2001 |
| WO | WO 01/32144 A1 | 5/2001 |
| WO | WO 02/11695 A3 | 2/2002 |
| WO | WO 02/054868 A2 | 7/2002 |
| WO | WO 02/055101 A2 | 7/2002 |
| WO | WO 02/087542 A1 | 11/2002 |

OTHER PUBLICATIONS

Maa, Y., et al., "Spray-Drying of Air-Liquid Interface Sensitive Recombinant Human Growth Hormone," *Journal of Pharmaceutical Sciences* vol. 87(2) :152-159 (1998).

Mumenthaler, M., et al., "Feasibility Study on Spray-Drying Protein Pharmaceuticals: Recombinant Human Growth Hormone and Tissue-Type Plasminogen Activator," *Pharmaceutical Research*, vol. 11(1):12-20 (1994).

Patton, J. and Platz, R., "(D) Routes of Delivery: Case Studies (2) Pulmonary Delivery of Peptides and Proteins for Systemic Action," *Advanced Drug Delivery Reviews*, 8:179-196 (1992).

Niven, R., "Delivery of Biotherapeutics by Inhalation] Aerosol," *Critical Reviews in Therapeutic Drug Carrier Systems*, 12(2&3) :151-231 (1995).

Lo et al., "Protein Location in Liposomes, A Drug Carrier: A Prediction by Differential Scanning Calorimetry," *Journal of Pharmaceutical Sciences*, 84(7) :805-814 (1995).

Vanbever et al., "Formulation and Physical Characterization of Large Porous Particles for Inhalation," *Pharmaceutical Research*, 16(11):1735-1742 (1999).

Edwards, "The Macrotransport of Aerosol Particles in The Lung: Aerosol Depositon Phenomena," *J. Aerosol Sci.*, 26(2):293-317 (1995).

Edwards et al., "Large Porous Particles for Pulmonary Drug Delivery," *Science*, 276:1868-1871 (1997).

French et al., "The Influence of Formulation on Emission, Deaggregation and Deposition of Dry Powders for Inhalation," *J. Aerosol Sci*, 27(5):769-783 (1996).

Hanes et al., "Porous Dry-Powder PLGA Microspheres Coated With Lung Surfactant for Systemic Insulin Delivery VIA The Lung," *Proceed Int'l. Symp. Control Rel. Bioact. Mater*, pp. 57-58 (1997).

Gupta et al., "Physical Characterization of Large Porous Particles for Inhalation," *Pharmaceutical Research*, (2000).

Vanbever et al., "Letter to the Editor", *Pharmaceutical Research*, (2000).

Mintzes, "The Spray Drying of Large, Porous Particles for Aerosol Drug Delivery to The Lung," *The Pennsylvania State University, University Scholars Program*, pp. 1-44, Thesis for baccalaureate degree (1998).

Wang et al., "Inhalation of Estradiol for Sustained Systemic Delivery," *J. of Aerosol Medicine*, 12(1):27-36 (1999).

Damgé, C., et al., "New Approach for Oral Administration of Insulin With Polyalkylcyanoacrylate Nanocapsules as Drug Carrier", *Diabetes*, 37:246-251 (1988).

Ben-Jebria et al., "Large Porous Particles for Sustained Protection from Carbachol-Induced Bronchoconstriction in Guinea Pigs", *Pharmaceutical Research*, 16(4) :555-561 (1999).

Andya et al., "The Effect of Formulation Excipients on Protein Stability and Aerosol Performance of Spray-Dried Powders of a Recombinant Humanized Anti-IgE Monoclonal Antibody," *Pharmaceutical Research*, 16(3) :350-358 (1999).

Broadhead, J., et al., "The Spray Drying of Pharmaceuticals," *Drug Development and Industrial Pharmacy*, 18(11&12):1169-1206 (1992).

Nice, "Aerosol Properties of Large, Porous Particles for Inhalation," *The Pennsylvania State University, University Scholars Program*, pp. 1-59, Thesis for baccalaureate degree, (1998).

Niven et al., "Abstracts for the International Society for Aerosols in Medicine $12^{th}$ Biennial Congress," *J. of Aerosol Med.*, 12(2) sec. 73 (1999).

Johnston et al., "Abstracts for the International Society for Aerosols in Medicine $12^{th}$ Biennial Congress," *J. of Aerosol Med.*, 12(2) sec. 84 (1999).

Scheuch et al., "Abstracts for the International Society for Aerosols in Medicine $12^{th}$ Biennial Congress," *J. of Aerosol Med.*, 12(2) sec. 138 (1999).

Li et al., "Aerodynamics and Aerosol Particle Deaggregation Phenomena In Model Oral-Pharyngeal Cavities," *J. Aerosol Sci.* 27(8):1269-1286 (1996).

Kawaguchi, H., et al., "Phagocytosis of Latex Particles by Leukocytes. I. Dependence of Phagocytosis on the Size and Surface Potential of Particles," *Biomaterials* 7:61-66 (1986).

Krenis, L.J. and B. Strauss, "Effect of Size and Concentration of Latex Particles on Respiration of Human Blood Leucocytes," *Proc. Soc. Exp. Med.*, 107:748-750 (1961).

Heyder, J., et al., "Deposition of Particles in the Human Respiratory Tract in the Size Range 0.005-15 µm," *J. Aerosol. Sci.*, 17(3) :811-825.

Visser, J., "An Invited Review: Van der Waals and Other Cohesive Forces Affecting Power Fludization", *Powder Technology*, 58:1-10 (1989).

Gonda, I., "Aerosols for Delivery of Therapeutic and Diagnostic Agents to the Respiratory Tract," in *Critical Reviews in Therapeutic Drug Carrier Systems*, 6:273-313 (1990).

Gonda, I., "Physico-chemical Principles in Aerosol Delivery," in *Topics in Pharmaceutical Sciences* 1991, Crommelin, D.J. and K.K. Midha, Eds., Medpharm Scientific Publishers, Stuttgart, pp. 95-117 (1992).

Morén, F., "Aerosol Dosage Forms and Formulations," in *Aerosols in Medicine. Principles, Diagnosis and Therapy*, Morén, et al., Eds, Elsevier, Amsterdam, 1985.

Heinemann, L., et al., "Time-action Profile of Inhaled Insulin," *Diabetic Medicine*, 14:63-72 (1997).

Abstract from: Derwent Info ltd., Access No. 1995-195390 / 199526.

Adjei, A., and Garren, J,, "Pulmonary Delivery of Peptide Drugs: Effect of Particle Size on Bioavailability of Leuprolide Acetate in Healthy Male Volunteers," *Pharm. Res.*, 7(6):565-569 (1990).

Allen, T.M., et al., "Subcutaneous Administration of Liposomes: A Comparison with the Intravenous and Intraperitoneal Routes of Injection," *Biochem. et Biophys. Acta.* 1150:9-16 (1993).

Altshuler, B., et al., "Aerosol Deposition in the Human Respiratory Tract," *Am. Med. Assoc. Arch. of Indust. Health* 15:293-303 (1957).

Anderson, P.J., et al., "Effect of Cystic Fibrosis on Inhaled Aerosol Boluses," *Am. Rev. Respir. Dis.*, 140:1317-1324 (1989).

Anderson, M., et al., "Human Deposition and Clearance of 6-μm Particles Inhaled with an Extremely Low Flow Rate," *Exp. Lung Res.*, 21:187-195 (1995).

Barrera, D.A., et al., "Synthesis and RGD Peptide Modification of a New Biodegradable Copolymer: Poly(lactic acid-co-lysine)," *J. Am. Chem. Soc.*, 115:11010-11011 (1993).

Beck, L.R., et al., "A New Long-Acting Injectable Microcapsule System for the Administration of Progesterone," *Fertility and Sterility*, 31(5):545-551 (1979).

Benita, S., et al., "Characterization of Drug-loaded Poly(d, l-lactide) Microspheres," *J. of Pharm. Sci* 73(12):1721-1724 (1984).

Blackett, P.M., and G. Buckton, "A Microcalorimetric Investigation of the Interaction of Surfactants with Crystalline and Partially Crystalline Salbutamol Sulphate in a Model Inhalation Aerosol System," *Pharmaceutical Research*, 12(11):1689-1693 (1995).

Brain, J.D., "Physiology and Pathophysiology of Pulmonary Macrophages". In *The Reticuloendothelial System*, Reichard and Filkins, eds. (Plenum Press, New York), pp. 315-327 (1985).

Brown, A.R., et al., "Propellant-Driven Aerosols of Functional Proteins as Potential Therapeutic Agents in the Respiratory Tract," *Immunopharmacology*, 28:241-257 (1994).

Byron, P.R., "Determinants of Drug and Polypeptide Bioavailability from Aerosols Delivered to the Lung," *Adv. Drug. Del. Rev.*, 5:107-132 (1990).

Carroll, B.A., et al., "Gelatin Encapsulated Nitrogen Microbubbles as Ultrasonic Contrast Agents," *Investigative Radiology*, 15:260-266 (1980).

Carroll, B.A., et al., "Ultrasonic Contrast Enhancement of Tissue by Encapsulated Microbubbles," *Radiology*, 143:747-750 (1982).

Ch'ng, H.S., et al., "Bioadhesive Polymers as Platforms for Oral Controlled Drug Delivery II: Synthesis and Evaluation of Some Swelling, Water-Insoluble Bioadhesive Polymers," *J. of Pharm Sci.*, 74(4):399-405 (1985).

Clark, A., and P. Byron, "Dependence of Pulmonary Absorption Kinetics on Aerosol Particle Size," *Z. Erkrank. Atm.org.*, 166:13-24 (1986).

Clark, A.R., and M. Egan, "Modeling the Deposition of Inhaled Powdered Drug Aerosols," *J. Aerosol Sci.*, 25(1):175-186 (1994).

Clay, M.M., et al. "Effect of Aerosol Particle Size on Bronchodilatation with Nebulised Terbutaline in Asthmatic Subjects," *Thorax* 41:364-368(1986).

Cohen, S., et al., "Controlled Delivery Systems for Proteins Based on Poly(Lactic/Glycolic Acid) Microspheres," *Pharm. Res.* 8(6):713-720(1991).

Colthorpe, P., et al., "The Pharmacokinetics of Pulmonary-Delivered Insulin: A Comparison of Intratracheal and Aerosol Administration to the Rabbit," *Pharm. Res.* 9(6):764-768 (1992).

Daly, W.H., et al., "The Preparation of N-Carboxyanhydrides of α-Amino Acids Using Bis(Trichloromethyl) Carbonate," *Tetrahedron Lett.*, 29(46):5859-5862 (1988).

Damms, B. and W. Bains, "The Cost of Delivering Drugs without Needles," *J. Controlled Release*, 8-11 (1996).

Darquenne, C., and M. Paiva, "Two and Three-Dimensional Simulations of Aerosol Transport and Deposition in Alveolar Zone of Human Lung," *Journal of Applied Physiology*, 80(4):1401-1414 (1996).

Davies, C.N., et al., "Breathing of Half-micron Aerosols. I. Experimental.," *J. of Appl. Physiol.* 32(5):591-600(1972).

Davis, S.S., and L. Illum, "Polymeric Microspheres as Drug Carriers," *Biomaterials*, 9:111-115 (1988).

Davis, S.S., et al., "Microspheres as Controlled-Release Systems for Parenteral and Nasal Administration," *Controlled Release Technology*, Chapter 15, pp. 201-213 (1987).

Dorries, A.M., and Valberg P.A., "Heterogeneity of Phagocytosis for Inhaled Versus Instilled Material," *Am. Rev. Respir. Dis.*, 146:831-837 (1992).

Eldridge, J. H.; et al., "Biodegradable Microspheres as a Vaccine Delivery System," *Mol. Immunol.*, 28(3):287-294 (1991).

Feinstein, S.B., et al., "Two-Dimensional Contrast Echocardiography I. In Vitro Development and Quantitative Analysis of Echo Contrast Agents," *JACC* 3 (1):14-20 (1984).

Ferin, J., et al., "Pulmonary Retention of Ultrafine and Fine Particles in Rats," *Am. J. Respir. Cell Mol. Biol.* 6:535-542 (1992).

Findeisen, W. "Uber Das Absetzen Kleiner, in Der Luft Suspendierter Teilchen in Der Menshlichen Lunge Bei Der Atmung," *Pflugers Arch. D. Ges. Physiol.* 236:367-379 (1935).

Ganderton, D., "The Generation of Respirable Clouds Form Coarse Powder Aggregates," *J. Biopharmaceutical Sciences*, 3(1/2):101-105 (1992).

Gehr, P. et al., "Surfactant and Inhaled Particles in the Conducting Airways: Structural, Stereological, and Biophysical Aspects," *Microscopy Res. And Tech.*, 26:423-436 (1993).

Gerrity, T.R., et al., "Calculated Deposition of Inhaled Particles in the Airway Generations of Normal Subjects," *J. Appl. Phys.*, 47(4):867-873 (1979).

Gonda, I., "Preface. Major Issues and Future Prospects in the Delivery of Therapeutic and Diagnostic Agents to the Respiratory Tract," *Adv. Drug Del. Rev.* 5:1-9 (1990).

Gonda, I., "Targeting by Deposition," in Pharmaceutical Inhalation Aersol Technology (ed. A.J. Hickey), Marcel Dekkar Inc., pp. 61-82, New York (1992).

Gurny, R., et al., "Bioadhesive Intraoral Release Systems: Design, Testing and Analysis," Biomaterials, 5:336-340 (1984).

Heyder, J., and G. Rudolf, "Mathematical models of particle deposition in the human respiratory tract," *J. Aerosol Sci.*, 15:697-707 (1984).

Heyder, J., et al., "Total Deposition of Aerosol Particles in the Human Respiratory Tract for Nose and Mouth Breathing," *J. Aerosol Sci.*, 6:311-328 (1975).

Hickey, A.J., et al., "Use of Particle Morphology to Influence the Delivery of Drugs from Dry Powder Aerosols," *J. Biopharmaceutical Sci.*, 3(½):107-113 (1992).

Hirano, S., et al., "Pulmonary Clearance and Toxicity of Zinc Oxide Instilled into the Rat Lung," *Arch. of Toxicology*, 63:336-342 (1989).

Hrkach, et al., "Synthesis of Poly(L-lactic acid-co-L-lysine) Graft Copolymers," *Macromolecules*, 28(13):4736-4739 (1995).

Hrkach, J.S., et al., "Poly(L-Lactic acid-co-amino acid) Graft Copolymers: A Class of Functional Biodegradable Biomaterials" in Hydrogels and Biodegradable Polymers for Bioapplications, ACS Symposium Series No. 627, Raphael M. Ottenbrite, et al., Eds., Americal Chemical Society, Chapter 8, pp. 93-101, 1996.

Illum, L., et al., "Bioadhesive Microspheres as a Potential Nasal Drug Delivery System," *Int. J. of Pharm.* 39:189-199 (1987).

Johnson, M.A., et al. "Delivery of Albuterol and Ipratrophiumbromide from Two Nebulizer Systems in Chronic Stable Asthma: Efficacy and Pulmonary Deposition," *Chest*, 96:6-10 (1989).

Kao, Y.J., and R.L. Juliano, "Interactions of Liposomes with the Reticuloendothelial System, Effects of Reticuloendothelial Blockade on the Clearance of Large Unilamellar Vesicles," *Biochimica et Biophys. Acta.* 677:453-461 (1981).

Kassem, N. M., and D. Ganderton, "The Influence of Carrier Surface on the Characteristics of Inspirable Powder Aerosols," *J. Pharm. Pharmacol.*, 42(Supp):11 (1990).

Kobayashi, S. et al., "Pulmonary Delivery of Salmon Calcitonin Dry Powders Containing Absorption Enhancers in Rats," *Pharm. Res.*, 13(1):80-83 (1996).

Kohler, D., "Aerosols for Systemic Treatment" *Lung*, Suppl: pp. 677-684 (1990).

Komada, F. et al., Intratracheal Delivery of Peptide and Protein Agents: Absorption from Solution and Dry Powder by Rat Lung, *J. Pharm. Sci.*, 83(6):863-867 (Jun. 1994).

Kricheldorf, H.R. "α-Aminoacid-N-Carboxy-Anhydrides and Related Heterocycles," Springer-Verlag, Berlin (1987).

Kwok, K.K., et al., "Production of 5-15 μm Diameter Alginate Polylysine Microcapsules by an Air Atomization Technique," Pharm. Res., 8(3):341-344 (1991).

Lai, Y-L., et al., "Sustained Bronchodilation with Isoproterenol Poly (Glycolide-co-Lactide) Microspheres," *Pharm. Res.*, 10(1):119-125 (1993).

Lai, W.C., et al., "Protection Against *Mycoplasma pulminosis* Infection by Genetic Vaccination," *DNA and Cell Biology*, 14(7):643-651 (1995).

Landahl, "On The Removal of Air-borne Droplets by the Human Respiratory Tract: I. The Lung," *Bull. Math. Biophys.*, 12:43-56 (1950).

Langer, R., "New Methods of Drug Delivery", *Science*, 249:1527-1533 (1990).

Le Corre, P., et al., "Preparation and Characterization of Bupivacaine-Loaded Polylactide and Polylactide-Co-Glycolide Microspheres," *Int. J. of Pharmaceutics*, 107:41-49 (1994).

Leone-Bay, A., et al., "Microsphere Formation in a Series of Derivatized α-Amino Acids: Properties, Molecular Modeling, and Oral Delivery of Salmon calcitonin," *J. of Med. Chem.*, 38(21):4257-4262 (1995).

Liu, F., et al., "Pulmonary Delivery of Free and Liposomal Insulin," *Pharm. Res.* 10(2):228-232 (1993).

Liu, W.R., et al., "Moisture-Induced Aggregation of Lyophilized Proteins in the Solid State," *Biotechnol. and Bioeng.*, 37:177-184 (1991).

Martonen, T.B., "Mathematical Model for the Selective Deposition of Inhaled Pharmaceuticals", *J. of Pharm. Sci.*, 82(12):1191-1198 (1993).

Masinde, L.E., and Hickey, A.J., "Aerosolized Aqueous Suspensions of Poly(L-Lactic Acid) Microspheres," *Int. J. of Pharmaceutics*, 100:123-131 (1993).

Mathiowitz, E., et al., "Novel Microcapsules for Delivery Systems," *Reactive Polymers*, 6:275-283 (1987).

Mathiowitz, E., et al., "Polyanhydride Microspheres. IV. Morphology and Characterization of Systems Made by Spray Drying," *J. of Appl. Polymer Sci.* 45:125-134 (1992).

Mathiowitz, E., et al., "Morphology of Polyanhydride Microsphere Delivery ASystems," *Scanning Microscopy*, 4(2):329-340 (1990).

Mathiowitz, E., and R. Langer, "Polyanhydride Microspheres as Drug Carriers I. Hot-Melt Microencapsulation," *J. of Controlled Release* 5:13-22 (1987).

Mathiowitz, E., et al., "Polyanhydride Microspheres as Drug Carriers. II. Microencapsulation by Solvent Removal," *J. of Appl. Polymer Sci.*, 35:755-774 (1988).

Ménache, M.G., et al., "Particle Inhalability Curves for Humans and Small Laboratory Animals," *Annals of Occupational Hygiene*, 39(3):317-328 (1995).

Morimoto, Y., and Adachi, Y., "Pulmonary Uptake of Liposomal Phosphatidylcholine Upon Intratracheal Administration to Rats," *Chem. Pharm. Bull.* 30(6):2248-2251 (1982).

Mulligan, R.C., "The Basic Science of Gene Therapy", *Science*, 260:926-932 (1993).

Newman, S.P., "Therapeutic Inhalation Agents and Devices," *Inhalation Therapy*, 76(5):194-207 (1984).

Newman, S.P., "Aerosol Deposition Considerations in Inhalation Therapy," *Chest*, 88(2):152S-160S (1985).

Niven, R.W., et al., "The Pulmonary Absorption of Aerosolized and Intratracheally Instilled rhG-CSF and monoPEGylated rhG-CSF," *Pharm. Res.*, 12(9):1343-1349 (1995).

Niven, R.W., et al., "Solute Absorption From the Airways of the Isolated Rat Lung. III. Absorption of Several Peptidase-Resistant, Synthetic Polypeptides: Poly-(2-Hydroxyethyl) -Aspartamides," *Pharm. Res.*, 7(10):990-994 (1990).

Niwa, T., et al., "Aerosolization of Lactide/Glycolide Copolymer (PLGA) Nanospheres for Pulmonary Delivery of Peptide-Drugs," *Yakugaku Zasshi*, 115(9):732-741 (1995).

Ogiwara, M., "Clearance and Maximum Removal Rate of Liposomes in Normal and Impaired Liver of Rat," *Gastroenterologia Japonica*, 19(1):34-40 (1984).

Okumura, K., et al., "Intratracheal Delivery of Insulin. Absorption from Solution and Aerosol by Rat Lung," *Int. J. Pharmaceutics*, 88:63-73 (1992).

Patton, J.S., et al., "Bioavailability of pulmonary delivered peptides and proteins: α-interferon, calcitonins and parathyriod hormones," *J. Controlled Release*, 28:79-85 (1994).

Pavia, D., "Lung Mucociliary Clearance". In *Aerosols and the Lung: Clinical and Experimental Aspects*, Clarke, S.W. and Pavia, D., eds. (Butterworths, London), pp. 127-155, (1984).

Peart, J. et al., "Multicomponent Particle Interactions in Dry Powder Aerosols," *J. Pharm. Res.* 14(11 Suppl):p. S142-S143 (Nov. 1997).

Pinkerton, K.E., et al., "Aerosolized Fluorescent Microspheres Detected in the Lung Using Confocal Scanning Laser Microscopy", *Microscopy Res. and Tech.*, 26:437-443 (1993).

Rudt, S., and R.H. Muller, "In Vitro Phagocytosis Assay of Nano- and Microparticles by Chemiluminescence. I. Effect of Analytical Parameters, Particle Size and Particle Concentration," *J. Contr. Rel.*, 22:263-271 (1992).

Rudt, S., et al., "In Vitro Phagocytosis Assay of Nano- and Microparticles by Chemiluminescence. IV. Effect of Surface Modification by Coating of Particles with Poloxamine and Antarox CO on the Phagocytic Uptake", *J. of Contr. Rel.* 25:123-132 (1993).

Ruffin, R.E., et al., "The Preferential Deposition of Inhaled Isoproterenol and Propranolol in Asthmatic Patients," *Chest* 80(6):904-907 (1981).

Sela, M., et al., "Multichain Polyamino Acids," *J. Am. Chem. Soc.*, 78:746-751 (1956).

Smith, A.L., and B. Ramsey, "Aerosol Administration of Antibiotics," *Respiration*, 62(suppl 1):19-24 (1995).

Smith, P.L., "Peptide Delivery via the Pulmonary Route: A Valid Approach for Local and Systemic Delivery," *J. of Contr. Rel.*, 46:99-106 (1997).

Strand, S.E., and L. Bergqvist, "Radiolabeled Colloids and Macromolecules in the Lymphatic System," *Critical Reviews in Therapeutic Drug Carrier Systems*, 6(3):211-238 (1989).

Swift, D., "The Oral Airway—A Conduit or Collector for Pharmaceutical Aerosols?" *Respiratory Drug Delivery IV*, 187-195 (1994).

Tabata, Y., et al., "Controlled Delivery Systems for Proteins Using Polyanhydride Microspheres," *Pharm. Res.* 10(4):487-496 (1993).

Tabata, Y., and Y. Ikada, "Effect of Surface Wettability of Microspheres on Phagocytosis," *J. of Colloid and Interface Sci.*, 127(1):132-140 (1989).

Tabata, Y., and Y. Ikada, "Macrophage Phagocytosis of Biodegradable Microspheres Composed of L-lactic Acid/glycolic Acid Homo- and Copolymers," *J. of Biomed. Mater. Res.*, 22:837-858 (1988).

Tabata, Y., and Ikada, Y., "Effect of Size and Surface Charge of Polymer Microspheres on Their Phagocytosis by Macrophage," *J. Biomed. Mater. Res.*, 22:837-843 (1988).

Taburet, A.M., and Schmit, B., "Pharmacokinetic Optimisation of Asthma Treatment," *Clin. Pharmacokinet.* 26(5):396-418 (1994).

Tansey, I.P., "The Challenges in the Development of Metered Dose Inhalation Aerosols Using Ozone-Friendly Propellants," *Spray Technol. & Market*, 4:26-29 (1994).

Timsina, M.P., et al., "Drug Delivery to the Respiratory Tract Using Dry Powder Inhalers," *Int. J. of Pharm.*, 101:1-13 (1994).

Turner, J.R., and S.V. Hering, "Greased and Oiled Substrates as Bounce-Free Impaction Surfaces," *J. Aerosol Sci.*, 18(2):215-224 (1987).

Wall, D.A., "Pulmonary Absorption of Peptides and Proteins," *Drug Delivery*, 2:1-20 (1995).

Warheit, D.B., and Hartsky, M.A., "Role of Alveolar Macrophage Chemotaxis and Phagocytosis in Pulmonary Clearance to Inhaled Particles: Comparisons Among Rodent Species," *Microscopy Res. and Tech.*, 26:412-422 (1993).

Weiner, Norman et al., "Liposomes as a Drug Delivery System," *Drug Development and Industrial Pharmacy*, 15(10):1523-1554 (1989).

Wheatley, M.A., et al., "Contrast Agents for Diagnostic Ultrasound: Development and Evaluation of Polymer-Coated Microbubbles," *Biomaterials* 11:713-717 (1990).

Wichert, B., and Rohdewald, P., "Low Molecular Weight PLA: A Suitable Polymer for Pulmonary Administered Microparticles?," *J. Microencapsulation*, 10(2):195-207 (1993).

Wong, M., and Suslick, K.S., "Sonochemically Produced Hemoglobin Microbubbles," *Mat. Res. Soc. Symp. Proc.*, 372:89-95 (1995).

Zanen, P., et al., "The Optimal Particle Size for β-adrenergic Aerosols in Mild Asthmatics", *Int. J. of Pharm.*, 107:211-217 (1994).

Zanen, P., et al., "The Optimal Particle Size for Parasympathicolytic Aerosols in Mild Asthmatics", *Int. J. of Pharm.*, 114:111-115 (1995).

Zeng, X.M., et al., "The Controlled Delivery of Drugs to the Lung," *Int. J. of Pharm.*, 124:149-164 (1995).

Zeng, X.M., et al., "Tetrandrine Delivery to the Lung: The Optimisation of Albumin Microsphere Preparation by Central Composite Design," *Int. J. of Pharm.*, 109:135-145 (1994).

Bailey, Leonard C., Chromatography, Chapter 33, Remington's Pharmaceutical Sciences (17$^{th}$ Ed. 1985) pp. 593, 604, 607, 608.

* cited by examiner

PARTICLES FOR INHALATION HAVING SUSTAINED RELEASE PROPERTIES

RELATED APPLICATION

This application is a continuation-in-part of application Ser. No. 09/383,054 filed on Aug. 25, 1999. The entire content of the above-referenced application is hereby incorporated by reference.

BACKGROUND OF THE INVENTION

Pulmonary delivery of bioactive agents, for example, therapeutic, diagnostic and and prophylactic agents provides an attractive alternative to, for example, oral, transdermal and parenteral administration. That is, pulmonary administration can typically be completed without the need for medical intervention (e.g., it can be self-administered), the pain often associated with injection therapy is avoided, and the amount of enzymatic and pH mediated degradation of the bioactive agent, frequently encountered with oral therapies, can be significantly reduced. In addition, the lungs provide a large mucosal surface for drug absorption and there is no first-pass liver effect of absorbed drugs. Further, it has been shown that high bioavailability of many molecules, for example, macromolecules, can be achieved via pulmonary delivery or inhalation. Typically, the deep lung, or alveoli, is the primary target of inhaled bioactive agents, particularly for agents requiring systemic delivery.

The release kinetics or release profile of a bioactive agent into the local and/or systemic circulation is a key consideration in most therapies, including those employing pulmonary delivery. That is, many illnesses or conditions require administration of a constant or sustained levels of a bioactive agent to provide an effective therapy. Typically, this can be accomplished through a multiple dosing regimen or by employing a system that releases the medicament in a sustained fashion.

However, delivery of bioactive agents to the pulmonary system typically results in rapid release of the agent following administration. For example, U.S. Pat. No. 5,997,848 to Patton et al. describes the rapid absorption of insulin following administration of a dry powder formulation via pulmonary delivery. The peak insulin level was reached in about 30 minutes for primates and in about 20 minutes for human subjects. Further, Heinemann, Traut and Heise teach in Diabetic Medicine 14:63-72 (1997) that the onset of action, assessed by glucose infusion rate, in healthy volunteers after inhalation was rapid with the half-maximal action reached in about 30 minutes.

As such, a need exists for formulations suitable for inhalation comprising bioactive agents and wherein the bioactive agent of the formulation is released in a sustained fashion into the systemic and/or local circulation.

SUMMARY OF THE INVENTION

This invention is based upon the unexpected discovery that complexation of a multivalent metal cation with a therapeutic, prophylactic or diagnostic agent carrying a negative, and therefore opposite charge to that of the cation, results in a sustained release profile of the agent upon pulmonary delivery.

The invention generally relates to a method for pulmonary delivery of therapeutic, prophylactic and diagnostic agents to a patient wherein the agent is released in a sustained fashion, and to a composition comprising particles suitable for use in the method. In a particular embodiment, the particles are in the form of dry powder. In particular, the invention relates to a method for the pulmonary delivery of a therapeutic, prophylactic or diagnostic agent comprising administering to the respiratory tract of a patient in need of treatment, prophylaxis or diagnosis an effective amount of particles comprising a multivalent metal cation which is complexed with a therapeutic, prophylactic or diagnostic agent or any combination thereof, a pharmaceutically acceptable carrier and optionally, a multivalent metal cation-containing component. The therapeutic, prophylactic or diagnostic agent has a charge which permits complexation with the cation upon association of the two. The total amount of multivalent metal cation present in the particles is more than 1% weight/weight of the total weight of the agent (% w/w). Release of the agent from the administered particles occurs in a sustained fashion.

In one embodiment, the complexation of the therapeutic, prophylactic or diagnostic agent and the oppositely charged multivalent metal cation can result from metal coordination, ionic complexation, salt bridges, hydrogen bonding or a combination thereof.

The particles suitable for use in the method can comprise a therapeutic, prophylactic or diagnostic agent which is complexed with a multivalent metal cation. The agent possesses a charge which allows it to undergo complexation with the metal cation upon association of the two. In a preferred embodiment, the charge of the agent upon complexation with the multivalent metal cation, prior to administration, is that which the agent possesses at pulmonary pH. In a particular embodiment, the particles are in the form of a dry powder.

For example, the particles suitable for pulmonary delivery can comprise a therapeutic, prophylactic or diagnostic agent which possesses an overall net negative charge, and is complexed with a multivalent metal cation. For example, the agent can be insulin and the multivalent metal cation can be zinc.

In a particular embodiment, the particles of the invention comprise more than one multivalent metal cation, more than one bioactive agent or both.

The particles, can further comprise a carboxylic acid which is distinct from the bioactive agent and metal cation. In one embodiment, the carboxylic acid includes at least two carboxyl groups. Carboxylic acids include the salts thereof as well as combinations of two or more carboxylic acids and/or salts thereof. In a preferred embodiment, the carboxylic acid is a hydrophilic carboxylic acid or salt thereof. Citric acid and citrates, such as, for example sodium citrate, are preferred. Combinations or mixtures of carboxylic acids and/or their salts also can be employed.

The particles suitable for use in the invention can further comprise an amino acid. In a preferred embodiment the amino acid is hydrophobic.

In a particular embodiment, the particles can be in the form of a dry powder suitable for inhalation. The particles can have a tap density of less than about 0.4 g/cm$^3$, preferably less than about 0.1 g/cm$^3$. Further, the particles suitable for use in the invention can have a median geometric diameter of from about 5 micrometers to about 30 micrometers. In yet another embodiment, the particles suitable for use in the invention have an aerodynamic diameter of from about 1 to about 5 microns.

The invention has numerous advantages. For example, particles suitable for inhalation can be designed to possess a sustained release profile. This sustained released profile provides for prolonged residence of the administered bioactive agent in the lung and thereby, increases the amount of time in which therapeutic levels of the agent are present in the local environment or systemic circulation. The sustained release of agent provides a desirable alternative to injection therapy currently used for many therapeutic, diagnostic and prophylactic agent requiring sustained release of agent, such as insulin for the treatment of diabetes. In addition, the invention provides a method of delivery to the pulmonary system wherein the high initial release or burst of agent typically seen in inhalation therapy is reduced. Consequently, patient compliance and comfort can be increased by not only reducing frequency of dosing, but by providing a therapy which is more amenable and efficacious to patients.

Figure 1A:
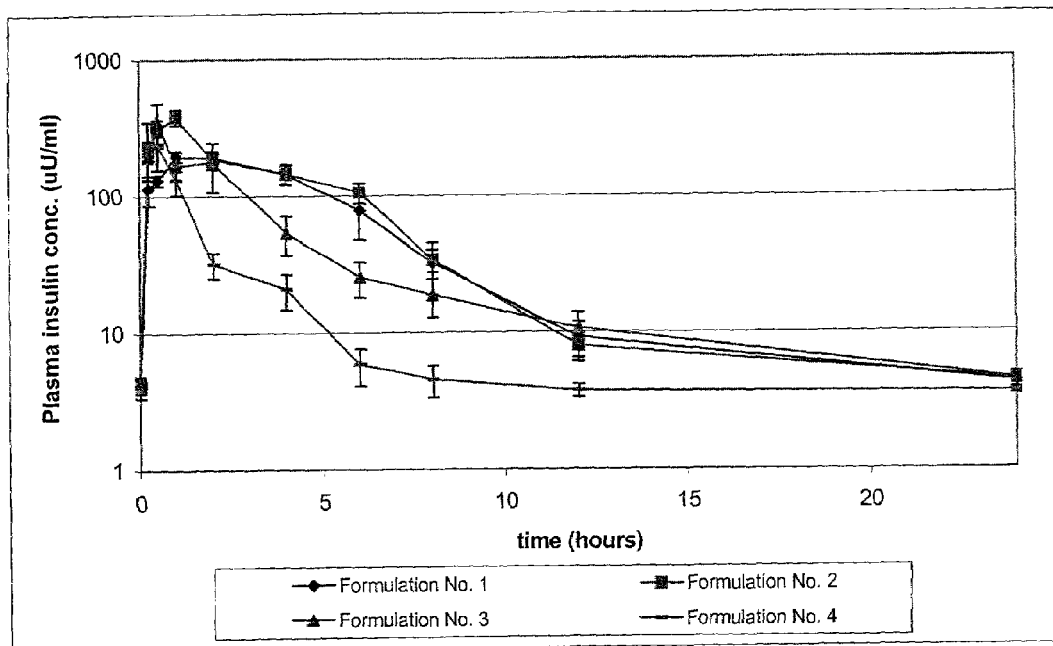
FIG. 1A is a graph of insulin concentration (μU/mL) in rat plasma versus time post administration of insulin powder Formulations 1-4.
Figure 1B:
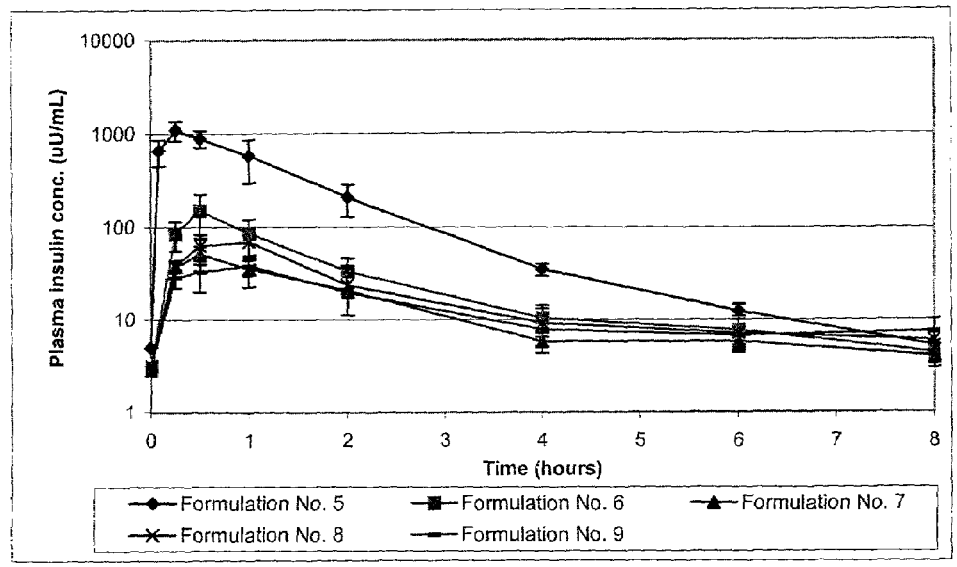
FIG. 1B is a graph of insulin concentration (μU/mL) in rat plasma versus time post administration of insulin powder Formulations 5-9. A reduction in the initial release is seen with sustained release Formulations 5-9 of the invention.
Figure 2:
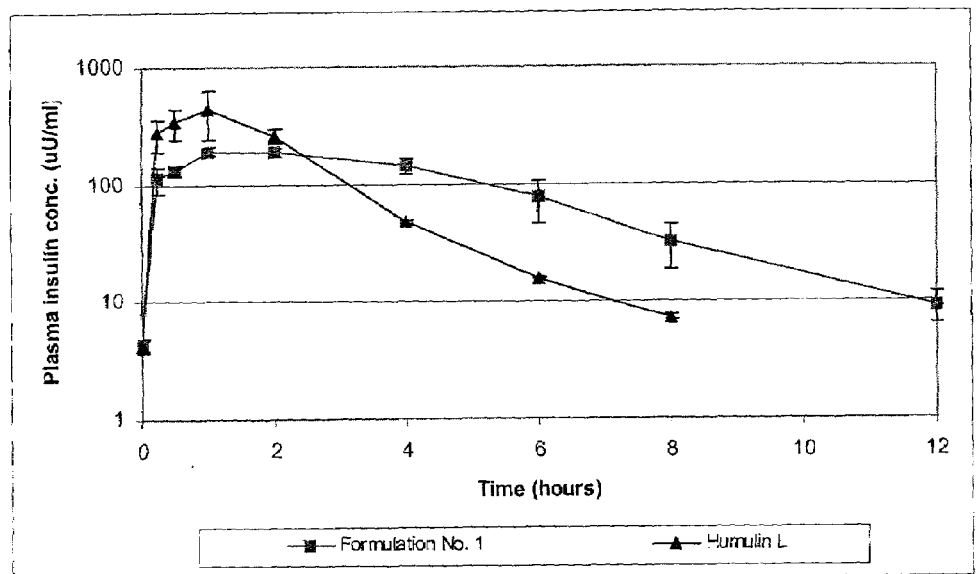
FIG. 2 is graph showing insulin concentration (μU/mL) in rat plasma versus time post administration of Formulation No. 1 and Humulin L.
Figure 3:
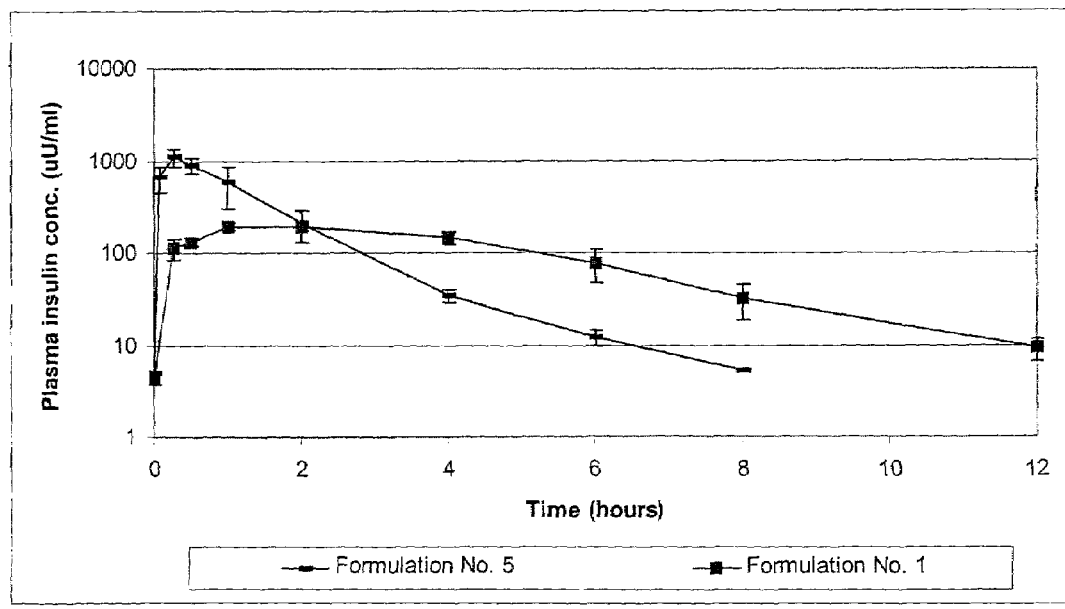
FIG. 3 is a graph of plasma insulin concentration (μU/mL) versus time post administration of Formulation No. 1 and the fast release Formulation No. 5.
Figure 4:
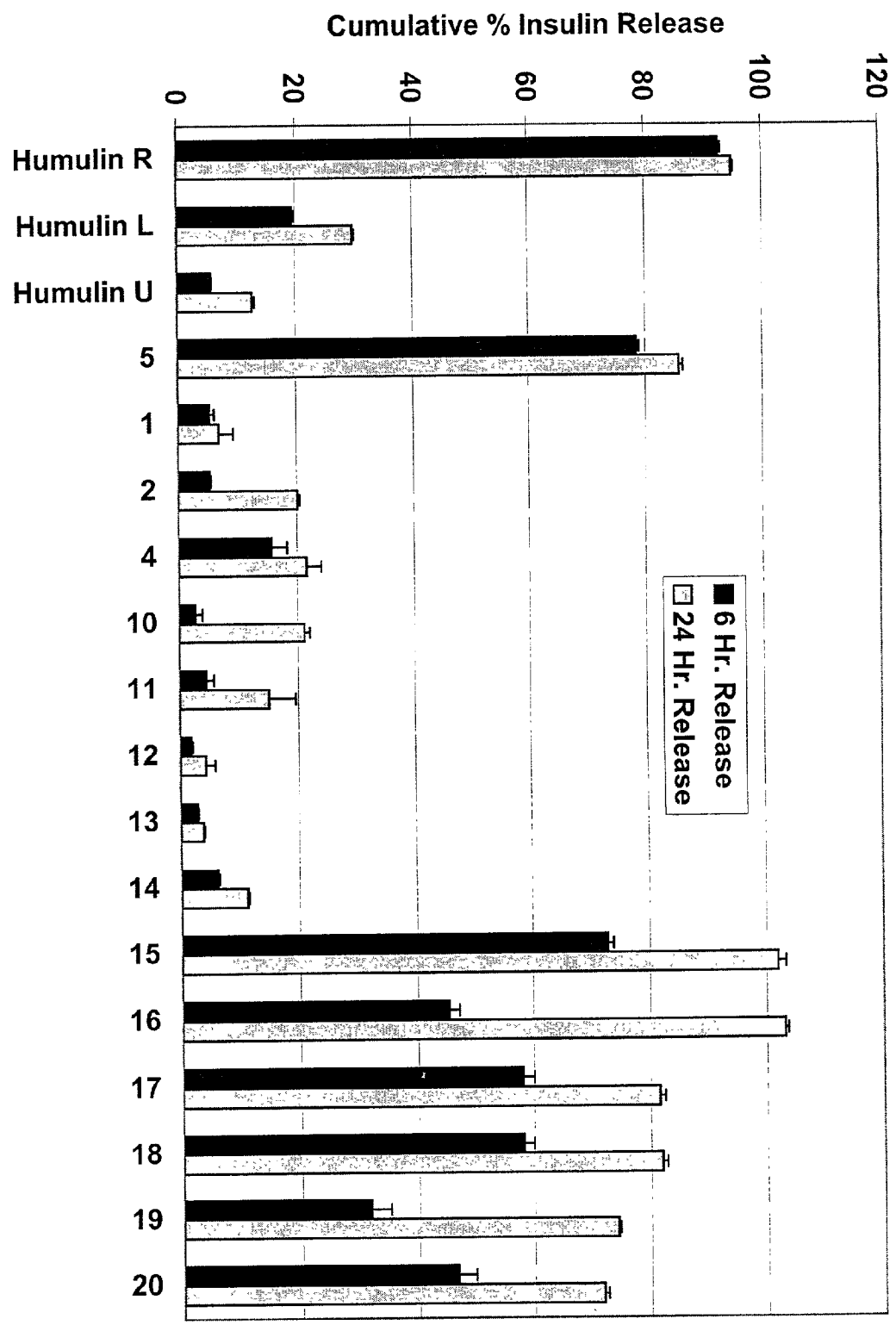
FIG. 4 is a graph of Cumulative % Recovery in vitro versus time for various formulations.

The foregoing and other objects, features and advantages of the invention will be apparent from the following more particular description of preferred embodiments of the invention.

DETAILED DESCRIPTION OF THE INVENTION

A description of preferred embodiments of the invention follows.

Therapeutic, prophylactic or diagnostic agents, can also be referred to herein as "bioactive agents", "medicaments" or "drugs".

The invention relates to a method for the pulmonary delivery of therapeutic, prophylactic and diagnostic agents comprising administering to the respiratory tract of a patient in need of treatment, prophylaxis or diagnosis an effective amount of particles comprising a multivalent metal cation which is complexed with a therapeutic, prophylactic or diagnostic agent or any combination thereof having a charge which permits complexation with the cation upon association with the agent, a pharmaceutically acceptable carrier and optionally, a multivalent metal cation-containing component wherein the total amount of multivalent metal cation present in the particles is more than 1% weight/weight of the total weight of the agent (% w/w). The agent is released from the administered particles in a sustained fashion. In a particular embodiment, the particles can be in the form of a dry powder.

The particles of the invention release bioactive agent in a sustained fashion. As such, the particles possess sustained release properties. "Sustained release", as that term is used herein, refers to a release of active agent in which the period of release of an effective level of agent is longer than that seen with the same bioactive agent which is not complexed with a multivalent metal cation, prior to administration. In addition, a sustained release also refers to a reduction in the burst of agent typically seen in the first two hours following administration, and more preferably in the first hour, often referred to as the "initial burst". In a preferred embodiment, the sustained release is characterized by both the period of release being longer in addition to a decreased initial burst. For example, a sustained release of insulin can be a release showing elevated serum levels of insulin at least 4 hours post administration, such as about 6 hours or more.

"Pulmonary delivery", as that term is used herein refers to delivery to the respiratory tract. The "respiratory tract", as defined herein, encompasses the upper airways, including the oropharynx and larynx, followed by the lower airways, which include the trachea followed by bifurcations into the bronchi and bronchioli (e.g., terminal and respiratory). The upper and lower airways are called the conducting airways. The terminal bronchioli then divide into respiratory bronchioli which then lead to the ultimate respiratory zone, namely, the alveoli, or deep lung. The deep lung, or alveoli, are typically the desired target of inhaled therapeutic formulations for systemic drug delivery.

Complexation of the multivalent metal cation with the therapeutic, prophylactic or diagnostic agent can result from metal coordination, ionic complexation, salt bridges, hydrogen bonding or a combination thereof.

In a particular embodiment, complexation of the therapeutic, prophylactic or diagnostic agent and the multivalent metal cation can be a result of ionic complexation or bonding.

The particles suitable for use in the method can comprise a therapeutic, prophylactic or diagnostic agent which is complexed with a multivalent metal cation wherein the charge of the agent is such that it is able to undergo complexation with the cation upon association, prior to administration.

For example, the particles suitable for pulmonary delivery can comprise a therapeutic, prophylactic or diagnostic agent which possesses an overall net negative charge at the time of complexation with a multivalent metal cation. For example, the agent can be insulin and the multivalent metal cation can be zinc.

"Pulmonary pH range", as that term is used herein, refers to the pH range which can be encountered in the lung of a patient. Typically, in humans, this range of pH is from about 6.4 to about 7.0, such as from 6.4 to about 6.7. pH values of the airway lining fluid (ALF) have been reported in "Comparative Biology of the Normal Lung", CRC Press, (1991) by R. A. Parent and range from 6.44 to 6.74)

"Multivalent metal cation" as that term is used herein, refers to metal cations which possess a valency of +2 or more. The multivalent metal cation can be chosen to have a charge opposite to that of the active agent when the multivalent metal cation and active agent are associated. Combinations of multivalent metal cation can be used.

Suitable multivalent metal cations include, but are not limited to, biocompatible multivalent metal cations.

It is understood that the multivalent metal cations suitable for complexation with an active agent of opposite charge can be any of the transition state metals of the periodic table, and the non-transition state metals, for example, calcium (Ca), zinc (Zn), cadmium (Cd), mercury (Hg), strontium (Sr), and barium (Ba). Divalent metal cations are preferred, such as, Zn(II), Ca(II), Cu(II), Mg(II), Ni(II), Co(II), Fe(II), Ag(II), Mn(II) or Cd(II).

The complexation of the multivalent metal cation with the bioactive agent of opposite charge can be achieved by associating, for example, mixing the bioactive agent in a suitable aqueous solvent with at least one suitable metal cation component under pH conditions suitable for complexation of the metal cation and the bioactive agent. Typically, the metal cation-complexed active agent will be in the form of a precipitate. Preferably, the precipitated metal cation-complexed active agent remains in the solid state throughout the process used to obtain the final particles for administration. In a preferred embodiment, the bioactive agent is complexed with $Zn^{+2}$. Most preferably, the $Zn^{-2}$ is complexed to insulin.

Suitable pH conditions to obtain complexation of a metal cation with a bioactive agent can be determined based on the pKa of the bioactive agent. That is, the pH of the system wherein complexation takes place should be adjusted based on the pKa of the active agent in order to impart a negative charge on the active agent. Suitable pH conditions are typically achieved through use of an aqueous buffer system as the solvent (e.g., citrate, phosphate, acetate, etc.). Adjustment to the desired pH can be achieved with addition of an acid or base as appropriate. Suitable solvents are those in which the bioactive agent and the metal cation component are each at least slightly soluble. For example, sodium citrate, acetate, and phosphate buffers.

For example, employing a protein as the active agent, the agent may be mixed with the metal cation component in a buffer system wherein the protein has a negative charge. Specifically, insulin, for example, may be mixed with the desired metal cation component in an aqueous buffer system (e.g. citrate, phosphate, acetate, etc.), the pH of the resultant solution then can be adjusted to a desired value using an appropriate base solution (e.g., 1 N NaOH). That is, the pH of the insulin metal cation component mixture can be adjusted to about pH 6.7. At this pH insulin molecules have a net negative charge (pI=5.5) and complexation of the metal cation component to the insulin achieves a precipitate of the metal cation complexed insulin.

The metal cation complexed bioactive agent is then mixed with a pharmaceutically acceptable carrier. Typically, the solution containing the precipitated metal cation complexed biologically active agent is mixed with a solution of the pharmaceutically acceptable carrier. Suitable pharmaceutically acceptable carriers and appropriate solvent systems for use with same are provided in detail below. The solvent is then removed from the resulting mixture. Solvent removal techniques include, for example, lyophilization, evaporation and spray drying. Spray drying of the resulting mixture is a preferred method of preparing the particles of the invention. Specific spray drying processes are discussed in detail below. It is preferred that the solid metal cation complexed biologically active agent remain in solid form throughout the processing of the final particles.

The total amount of multivalent metal cation present in the particles of the invention is more than 1% by weight of the total weight of the active agent (% w/w), such as, about 2%, about 3%, about 4%, about 5% etc. For example, the ratio of multivalent cation to active agent present in the particles of the invention can be more than 1% w/w and range from about 1.5% w/w to about 2% w/w, or from about 2% w/w to about 2.5% w/w, or from about 2.5% w/w to about 3% w/w etc. . . . . It is understood that the upper limit of cation present depends upon the tolerance of the formulation by the recipient. For example, the formulation can have the multivalent metal cation present at about 50%, 100%, 150%, 200%, 250% by weight of the total weight of the active agent.

"Total amount of multivalent metal cation" refers to the entire concentration of multivalent metal cation within the particles. As such, the total amount of multivalent metal cation includes both multivalent metal cation which is complexed with the biologically active agent, as well as any multivalent metal cation which is present but not complexed with the biologically active agent. For example, the multivalent metal cation which is not associated with the active agent can be present, for example, as the metal cation of a metal cation-containing component, such as a multivalent metal cation-containing salt.

Suitable multivalent metal cation-containing components include, but are not limited to, salts having the multivalent metal cations described above and a suitable pharmaceutically acceptable counterion. The counterion can be, for example, chloride, bromide, citrate, tartrate, lactate, methanesulfonate, acetate, sulfonate formate, maleate, fumarate, malate, succinate, malonate, sulfate, phosphate, hydrosulfate, pyruvate, mucate, benzoate, glucuronate, oxalate, ascorbate, the conjugate base of a fatty acid (e.g., oleate, laurate, myristate, stearate, arachidate, behenate, arachidonate) and combinations thereof.

The particles of the invention comprise a pharmaceutically acceptable carrier. Suitable pharmaceutically acceptable carriers can be chosen, for example, based on achieving particles having the proper characteristics for inhalation to the area of the respiratory tract where delivery is desired and therapeutic action is achieved.

In a preferred embodiment of the invention, the pharmaceutically acceptable carrier of the particles is a phospholipid. Examples of suitable phospholipids include, among others, phosphatidic acids, phosphatidylcholines, phosphatidylalkanolamines such as a phosphatidylethanolamines, phosphatidylglycerols, phosphatidylserines, phosphatidylinositols and combinations thereof.

Specific examples of phospholipids include, 1,2-diacyl-sn-glycero-3-phosphocholine and a 1,2-diacyl-sn-glycero-3-phosphoalkanolamine phospholipids. Suitable examples of 1,2-diacyl-sn-glycero-3-phosphocholine phospholipids include, but are not limited to, 1,2-dipalmitoyl-sn-glycero-3-phosphocholine (DPPC), 1,2-distearoyl-sn-glycero-3-phosphocholine (DSPC), 1,2-dilaureoyl-sn-3-glycero-phosphocholine (DLPC), 1,2-dimyristoyl-sn-glycero-3-phosphocholine (DMPC), 1,2-dioleoyl-sn-glycero-3-phosphocholine (DOPC).

Suitable examples of 1,2-diacyl-sn-glycero-3-phosphoalkanolamine phospholipids include, but are not limited to, 1,2-dipalmitoyl-sn-glycero-3-ethanolamine (DPPE), 1,2-dimyristoyl-sn-glycero-3-phosphoethanolamine (DMPE), 1,2-distearoyl-sn-glycero-3-phosphoethanolamine (DSPE), 1,2-dilauroyl-sn-glycero-3-phosphoethanolamine (DLPE), and 1,2-dioleoyl-sn-glycero-3-phosphoethanolamine (DOPE).

Other classes of phospholipids suitable for use in the invention as a pharmaceutically acceptable carrier include 1,2-diacyl-sn-glycero-3-alkylphosphocholines and 1,2-diacyl-sn-glycero-3-alkylphosphoalkanolamines.

Specific examples of 1,2-diacyl-sn-glycero-3-alkylphosphocholine phospholipids include, but are not limited to, 1,2-dipalmitoyl-sn-glycero-3-ethylphosphocholine (DPePC), 1,2-dimyristoyl-sn-glycero-3-ethylphosphocholine (DMePC), 1,2-distearoyl-sn-glycero-3-ethylphosphocholine (DSePC), 1,2-dilauroyl-sn-glycero-3-ethylphosphocholine (DLePC), and 1,2-dioleoyl-sn-glycero-3-ethylphosphocholine (DOePC).

Specific examples of 1,2-diacyl-sn-glycero-3-alkylphosphoalkanolamines include, but are not limited to 1,2-dipalmitoyl-sn-glycero-3-ethylethanolamine (DPePE), 1,2-dimyristoyl-sn-glycero-3-ethylphosphoethanolamine (DMePE), 1,2-distearoyl-sn-glycero-3-ethylphosphoethanolamine (DSePE), 1,2-dilauroyl-sn-glycero-3-ethylphosphoethanolamine (DLePE), and 1,2-dioleoyl-sn-glycero-3-ethylphosphoethanolamine (DOePE).

Other phospholipids are known to those skilled in the art and are described in U.S. patent application Ser. No. 09/752, 109 entitled "Particles for Inhalation Having Sustained Release Properties" filed on Dec. 29, 2000 and U.S. patent application Ser. No. 09/752,106 entitled "Particles for Inhalation Having Sustained release Properties" filed on Dec. 29, 2000 the contents of all of which are incorporated herein in their entirety. In a preferred embodiment, the phospholipids are endogenous to the lung.

The phospholipid, can be present in the particles in an amount ranging from about 0 to about 90 weight %. More commonly it can be present in the particles in an amount ranging from about 10 to about 60 weight %.

In another embodiment of the invention, the phospholipids or combinations thereof are selected to impart controlled release properties to the highly dispersible particles. The phase transition temperature of a specific phospholipid can be below, around or above the physiological body temperature of a patient. Preferred phase transition temperatures range from 30° C. to 50° C., (e.g., within ±10 degrees of the normal body temperature of patient). By selecting phospholipids or combinations of phospholipids according to their phase transition temperature, the particles can be tailored to have controlled release properties. For example, by administering particles which include a phospholipid or combination of phospholipids which have a phase transition temperature higher than the patient's body temperature, the release of active agent can be slowed down. On the other hand, rapid release can be obtained by including in the particles phospholipids having lower transition temperatures. Particles having controlled release properties and methods of modulating release of a biologically active agent are described in U.S. patent application Ser. No. 09/644,736 entitled Modulation of Release From Dry Powder Formulations by Controlling Matrix Transition, filed on Aug. 23, 2000, the entire contents of which are incorporated herein by reference.

In another embodiment, the particles of the invention do not include a pharmaceutically acceptable carrier. For example, the dry powder for use in the invention comprises a multivalent metal cation which is complexed with a therapeutic, prophylactic or diagnostic agent or any combination thereof having a charge which permits complexation with the cation upon association with the agent and optionally, a multivalent metal cation-containing component wherein the total amount of multivalent metal cation present in the dry powder is more than 1% weight/weight of the total weight of the agent (% w/w).

Therapeutic, prophylactic or diagnostic agents, can also be referred to herein as "bioactive agents", "medicaments" or "drugs". It is understood that one or more bioactive agents can be present in the particles of the invention. Hydrophilic as well as hydrophobic agents can be used. The agent must be capable of possessing a charge which allows it to undergo complexation with the metal cation.

The amount of bioactive agent present in the particles of the invention can be from about 0.1 weight % to about 95 weight %. For example, from about 1 to about 50%, such as from about 5 to about 30%. Particles in which the drug is distributed throughout a particle are preferred.

Suitable bioactive agents include agents which can act locally, systemically or a combination thereof. The term "bioactive agent," as used herein, is an agent, or its pharmaceutically acceptable salt, which when released in vivo, possesses the desired biological activity, for example therapeutic, diagnostic and/or prophylactic properties in vivo.

Examples of bioactive agent include, but are not limited to, proteins and peptides, polysaccharides and other sugars, lipids, and DNA and RNA nucleic acid sequences having therapeutic, prophylactic or diagnostic activities. Agents with a wide range of molecular weight can be used.

The agents can have a variety of biological activities, such as vasoactive agents, neuroactive agents, hormones, anticoagulants, immunomodulating agents, cytotoxic agents, prophylactic agents, diagnostic agents, antibiotics, antivirals, antisense, antigens, antineoplastic agents and antibodies.

Proteins, include complete proteins, muteins and active fragments thereof, such as insulin, immunoglobulins, antibodies, cytokines (e.g., lymphokines, monokines, chemokines), interleukins, interferons ($\beta$-IFN, $\alpha$-IFN and $\gamma$-IFN), erythropoietin, somatostatin, nucleases, tumor necrosis factor, colony stimulating factors, enzymes (e.g. superoxide dismutase, tissue plasminogen activator), tumor suppressors, blood proteins, hormones and hormone analogs (e.g., growth hormone, such as human growth hormone (hGH), adrenocorticotropic hormone and luteinizing hormone releasing hormone (LHRH)), vaccines (e.g., tumoral, bacterial and viral antigens), antigens, blood coagulation factors; growth factors; granulocyte colony-stimulating factor ("G-CSF"); peptides include parathyroid hormone-related peptide, protein inhibitors, protein antagonists, and protein agonists, calcitonin; nucleic acids include, for example, antisense molecules, oligonucleotides, and ribozymes. Polysaccharides, such as heparin, can also be administered.

Bioactive agents for local delivery within the lung, include agents such as those for the treatment of asthma, chronic obstructive pulmonary disease (COPD), emphysema, or cystic fibrosis. For example, genes for the treatment of diseases such as cystic fibrosis can be administered, as can beta agonists, steroids, anticholinergics, and leukotriene modifiers for asthma.

Nucleic acid sequences include genes, oligonucleotides, antisense molecules which can, for instance, bind to complementary DNA to inhibit transcription, and ribozymes.

The particles can further comprise a carboxylic acid which is distinct from the metal cation complexed biologically active agent. In one embodiment, the carboxylic acid includes at least two carboxyl groups. Carboxylic acids include the salts thereof as well as by combinations of two or more carboxylic acids and/or salts thereof In a preferred embodiment, the carboxylic acid is a hydrophilic carboxylic acid or salt thereof. Suitable carboxylic acids include but are not limited to hydroxydicarboxylic acids, hydroxytricarboxylic acids and the like. Citric acid and citrates, such as, for example sodium citrate, are preferred. Combinations or mixtures of carboxylic acids and/or their salts also can be employed.

The carboxylic acid can be present in the particles in an amount ranging from about 0 to about 80% weight. Preferably, the carboxylic acid can be present in the particles in an amount of about 10 to about 20%.

The particles suitable for use in the invention can further comprise an amino acid. In a preferred embodiment the amino acid is hydrophobic. Suitable naturally occurring hydrophobic amino acids, include but are not limited to, leucine, isoleucine, alanine, valine, phenylalanine, glycine and tryptophan. Combinations of hydrophobic amino acids can also be employed. Non-naturally occurring amino acids include, for example, beta-amino acids. Both D, L configurations and racemic mixtures of hydrophobic amino acids can be employed. Suitable hydrophobic amino acids can also include amino acid derivatives or analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1-C8 hydrocarbons which are completely saturated, which contain one or two heteroatoms such as nitrogen, oxygen or sulfur and/or which contain one or more units of unsaturation. Aromatic or aryl groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F)—O (aliphatic, substituted aliphatic, benzyl, substituted benzyl, aryl or substituted aryl group), —CN, —$NO_2$, —COOH, —$NH_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO(aliphatic group, substituted aliphatic, benzyl, substituted benzyl, aryl or substituted aryl group), —$CONH_2$, —CONH(aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(=NH)—$NH_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lipophilicity or hydrophobicity of natural amino acids which are hydrophilic.

A number of the suitable amino acids, amino acid analogs and salts thereof can be obtained commercially. Others can be synthesized by methods known in the art. Synthetic techniques are described, for example, in Green and Wuts, "*Protecting Groups in Organic Synthesis*", John Wiley and Sons, Chapters 5 and 7, 1991.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale has a value greater or equal to 0.5, in other words, has a tendency to partition in the nonpolar acid which is at least equal to that of glycine.

Examples of amino acids which can be employed include, but are not limited to: glycine, proline, alanine, cysteine, methionine, valine, leucine, tyrosine, isoleucine, phenylalanine, tryptophan. Preferred hydrophobic amino acids include leucine, isoleucine, alanine, valine, phenylalanine, glycine and tryptophan. Combinations of hydrophobic amino acids can also be employed. Furthermore, combinations of hydrophobic and hydrophilic (preferentially partitioning in water) amino acids, where the overall combination is hydrophobic, can also be employed. Combinations of one or more amino acids can also be employed.

The amino acid can be present in the particles of the invention in an amount of from about 0% to about 60 weight %. Preferably, the amino acid can be present in the particles in an amount ranging from about 5 to about 30 weight %. The salt of a hydrophobic amino acid can be present in the particles of the invention in an amount of from about 0% to about 60 weight %. Preferably, the amino acid salt is present in the particles in an amount ranging from about 5 to about 30 weight %. Methods of forming and delivering particles which include an amino acid are described in U.S. patent application Ser. No. 09/382,959, filed on Aug. 25, 1999, entitled "Use of Simple Amino Acids to Form Porous Particles During Spray Drying" the entire teaching of which is incorporated herein by reference.

In a further embodiment, the particles can also include other excipients such as, for example, buffer salts, dextran, polysaccharides, lactose, trehalose, cyclodextrins, proteins, polycationic complexing agents, peptides, polypeptides, fatty acids, fatty acid esters, inorganic compounds, phosphates. It is understood, however, that in certain embodiments, the particles are in the substantial absence of the polycationic complexing agent, protamine.

In one embodiment of the invention, the particles can further comprise polymers. Biocompatible or biodegradable polymers are preferred. Such polymers are described, for example, in U.S. Pat. No. 5,874,064, issued on Feb. 23, 1999 to Edwards et al., the teachings of which are incorporated herein by reference in their entirety.

In yet another embodiment, the particles include a surfactant other than the phospholipids described above. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to particles, they tend to present moieties to the external environment that do not attract similarly-coated particles, thus reducing particle agglomeration. Surfactants may also promote absorption of a therapeutic or diagnostic agent and increase bioavailability of the agent.

Suitable surfactants which can be employed in fabricating the particles of the invention include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxamer; a sorbitan fatty acid ester such as sorbitan trioleate (Span 85); Tween 80 and tyloxapol.

The surfactant can be present in the particles in an amount ranging from about 0 to about 5 weight %. Preferably, it can be present in the particles in an amount ranging from about 0.1 to about 1.0 weight %.

It is understood that when the particles include a carboxylic acid, an amino acid, a surfactant or any combination thereof, interaction between these components of the particle and the multivalent metal cation component can occur.

The particles, also referred to herein as powder, can be in the form of a dry powder suitable for inhalation. In a particular embodiment, the particles can have a tap density of less than about 0.4 g/cm$^3$. Particles which have a tap density of less than about 0.4 g/cm$^3$ are referred to herein as "aerodynamically light particles". More preferred are particles having a tap density less than about 0.1 g/cm$^3$.

Aerodynamically light particles have a preferred size, e.g., a volume median geometric diameter (VMGD) of at least about 5 microns (μm). In one embodiment, the VMGD is from about 5 μm to about 30 μm. In another embodiment of the invention, the particles have a VMGD ranging from about 9 μm to about 30 μm. In other embodiments, the particles have a median diameter, mass median diameter (MMD), a mass median envelope diameter (MMED) or a mass median geometric diameter (MMGD) of at least 5 µm, for example from about 5 µm to about 30 µm.

Aerodynamically light particles preferably have "mass median aerodynamic diameter" (MMAD), also referred to herein as "aerodynamic diameter", between about 1 µm and about 5 µm. In one embodiment of the invention, the MMAD is between about 1 µm and about 3 µm. In another embodiment, the MMAD is between about 3 µm and about 5 µm.

In another embodiment of the invention, the particles have an envelope mass density, also referred to herein as "mass density" of less than about 0.4 g/cm$^3$. The envelope mass density of an isotropic particle is defined as the mass of the particle divided by the minimum sphere envelope volume within which it can be enclosed.

Tap density can be measured by using instruments known to those skilled in the art such as the Dual Platform Microprocessor Controlled Tap Density Tester (Vankel, N.C.) or a GeoPyc™ instrument (Micrometrics Instrument Corp., Norcross, Ga. 30093). Tap density is a standard measure of the envelope mass density. Tap density can be determined using the method of USP Bulk Density and Tapped Density, United States Pharmacopia convention, Rockville, Md., 10$^{th}$ Supplement, 4950-4951, 1999. Features which can contribute to low tap density include irregular surface texture and porous structure.

The diameter of the particles, for example, their VMGD, can be measured using an electrical zone sensing instrument such as a Multisizer IIe, (Coulter Electronic, Luton, Beds, England), or a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition within targeted sites within the respiratory tract.

Experimentally, aerodynamic diameter can be determined by employing a gravitational settling method, whereby the time for an ensemble of particles to settle a certain distance is used to determine the aerodynamic diameter of the particles. An indirect method for measuring the mass median aerodynamic diameter (MMAD) is the multi-stage liquid impinger (MSLI). Specific instruments which can be employed to determine aerodynamic diameters include those known under the name of Aerosizer™ (TSI, Inc., Amherst, Mass.) or under the name of Anderson Cascade Impactor (Anderson Inst., Sunyra, Gas.).

The aerodynamic diameter, $d_{aer}$, can be calculated from the equation:

$$d_{aer}=d_g\sqrt{\rho_{tap}}$$

where $d_g$ is the geometric diameter, for example the MMGD and ρ is the powder density.

Particles which have a tap density less than about 0.4 g/cm$^3$, median diameters of at least about 5 µm, and an aerodynamic diameter of between about 1 µm and about 5 µm, preferably between about 1 µm and about 3 µm, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those currently used for inhalation therapies.

In comparison to smaller particles the larger aerodynamically light particles, preferably having a VMGD of at least about 5 µm, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 µm. Kawaguchi, H., et al, *Biomaterials* 7:61-66 (1986); Krenis, L. J. and Strauss, B., *Proc. Soc. Exp. Med.*, 107:748-750 (1961); and Rudt, S. and Muller, R. H., *J Contr. Rel.*, 22:263-272 (1992). For particles of statistically isotropic shape, such as spheres with rough surfaces, the particle envelope volume is approximately equivalent to the volume of cytosolic space required within a macrophage for complete particle phagocytosis.

The particles may be fabricated with the appropriate material, surface roughness, diameter and tap density for localized delivery to selected regions of the respiratory tract such as the deep lung or upper or central airways. For example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to about 5 µm are preferred for delivery to the central and upper airways. Particles having an aerodynamic diameter ranging from about 1 to about 3 µm are preferred for delivery to the deep lung.

Inertial impaction and gravitational settling of aerosols are predominant deposition mechanisms in the airways and acini of the lungs during normal breathing conditions. Edwards, D. A., *J Aerosol Sci.*, 26:293-317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 µm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95-117, Stuttgart: Medpharm Scientific Publishers, 1992)), by the formula:

$$d_{aer}=d\sqrt{\rho}$$

where the envelope mass p is in units of g/cm$^3$. Maximal deposition of monodispersed aerosol particles in the alveolar region of the human lung (~60%) occurs for an aerodynamic diameter of approximately $d_{aer}$=3 µm. Heyder, J. et al., *J Aerosol Sci.*, 17: 811-825 (1986). Due to their small envelope mass density, the actual diameter d of aerodynamically light particles comprising a monodisperse inhaled powder that will exhibit maximum deep-lung deposition is:

$$d=3/\sqrt{\rho}\ \mu m\ (\text{where } \rho<1\ g/cm^3);$$

where d is always greater than 3 µm. For example, aerodynamically light particles that display an envelope mass density, p=0.1 g/cm$^3$, will exhibit a maximum deposition for particles having envelope diameters as large as 9.5 µm. The increased particle size diminishes interparticle adhesion forces. Visser, J., *Powder Technology*, 58:1-10. Thus, large particle size increases efficiency of aerosolization to the deep lung for particles of low envelope mass density, in addition to contributing to lower phagocytic losses.

The aerodynamic diameter can be calculated to provide for maximum deposition within the lungs, previously achieved by the use of very small particles of less than about five microns in diameter, preferably between about one and about three microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

Suitable particles can be fabricated or separated, for example by filtration or centrifugation, to provide a particle sample with a preselected size distribution. For example, greater than about 30%, 50%, 70%, or 80% of the particles in a sample can have a diameter within a selected range of at least about 5 µm. The selected range within which a certain percentage of the particles must fall may be for example, between about 5 and about 30 µm, or optimally between about 5 and about 15 µm. In one preferred embodiment, at least a portion of the particles have a diameter between about 6 and about 11 µm. Optionally, the particle sample also can be fabricated wherein at least about 90%, or optionally about 95% or about 99%, have a diameter within the selected range. The presence of the higher proportion of the aerodynamically light, larger diameter particles in the particle sample enhances the delivery of therapeutic or diagnostic agents incorporated therein to the deep lung. Large diameter particles generally mean particles having a median geometric diameter of at least about 5 µm.

The particles can be prepared by spray drying. For example, a spray drying mixture, also referred to herein as "feed solution" or "feed mixture", which includes the bioactive agent in association with a multivalent metal cation, for example, complexed, a pharmaceutically acceptable carrier and optionally a multivalent metal cation component are fed to a spray dryer.

For example, complexation of the multivalent metal cation with the bioactive agent of opposite charge can be achieved by mixing the bioactive agent in a suitable aqueous solvent with at least one suitable metal cation component under pH conditions suitable for forming a complex of metal cation and bioactive agent. Typically, the metal cation-complexed active agent will be in the form of a precipitate. Preferably, the precipitated metal cation-complexed active agent remains in the solid state throughout the process used to obtain the final particles for administration. In a prefered embodiment, the bioactive agent is complexed with $Zn^{+2}$. Most preferably, the $Zn^{+2}$ is complexed to insulin.

Suitable pH conditions to form a metal cation complexed bioactive agent can be determined based on the pKa of the bioactive agent. That is, the pH of the system wherein complexation takes place should be adjusted based on the pKa of the active agent in order to impart a negative charge on the active agent. Suitable pH conditions are typically achieved through use of an aqueous buffer system as the solvent (e.g., citrate, phosphate, acetate, etc.). Adjustment to the desired pH can be achieved with addition of an acid or base as appropriate. Suitable solvents are those in which the bioactive agent and the metal cation component are each at least slightly soluble. For example, sodium citrate, acetate, and phosphate buffer systems.

The metal cation complexed bioactive agent is then mixed with a pharmaceutically acceptable carrier, as described above. Suitable organic solvents can be used to form a solution of the pharmaceutically acceptable carrier. Alternatively an aqueous solvent can be used to solubilize the carrier or a combination of aqueous and organic solvent can be employed. Suitable organic solvents include, but are not limited to, alcohols for example, ethanol, methanol, propanol, isopropanol, butanols, and others. Other organic solvents include, but are not limited to, perfluorocarbons, dichloromethane, chloroform, ether, ethyl acetate, methyl tert-butyl ether and others. Aqueous solvents that can be present in the feed mixture include water and buffered solutions. Both organic and aqueous solvents can be present in the spray-drying mixture fed to the spray dryer. In one embodiment, an ethanol water solvent is preferred with the ethanol:water ratio ranging from about 50:50 to about 90:10. The mixture can have a neutral, acidic or alkaline pH. Optionally, a pH buffer can be included. Preferably, the pH can range from about 3 to about 10.

The total amount of solvent or solvents being employed in the mixture being spray dried generally is greater than 99 weight percent. The amount of solids (drug, charged lipid and other ingredients) present in the mixture being spray dried generally is less than about 1.0 weight percent. Preferably, the amount of solids in the mixture being spray dried ranges from about 0.05% to about 0.5% by weight.

Using a mixture which includes an organic and an aqueous solvent in the spray drying process allows for the combination of hydrophilic and hydrophobic components, while not requiring the formation of liposomes or other structures or complexes to facilitate solubilization of the combination of such components within the particles.

Suitable spray-drying techniques are described, for example, by K. Masters in "Spray Drying Handbook", John Wiley & Sons, New York, 1984. Generally, during spray-drying, heat from a hot gas such as heated air or nitrogen is used to evaporate the solvent from droplets formed by atomizing a continuous liquid feed. Other spray-drying techniques are well known to those skilled in the art. In a preferred embodiment, a rotary atomizer is employed. An example of a suitable spray dryer using rotary atomization includes the Mobile Minor spray dryer, manufactured by Niro, Inc., Denmark. The hot gas can be, for example, air, nitrogen or argon.

Preferably, the particles of the invention are obtained by spray drying using an inlet temperature between about 100° C. and about 400° C. and an outlet temperature between about 50° C. and about 130° C.

The spray dried particles can be fabricated with a rough surface texture to reduce particle agglomeration and improve flowability of the powder. The spray-dried particle can be fabricated with features which enhance aerosolization via dry powder inhaler devices, and lead to lower deposition in the mouth, throat and inhaler device.

The particles of the invention can be employed in compositions suitable for drug delivery via the pulmonary system. For example, such compositions can include the metal cation complexed biologically active agent and a pharmaceutically acceptable carrier for administration to a patient, preferably for administration via inhalation. The particles can be co-delivered with larger carrier particles, not including a therapeutic agent, the latter possessing mass median diameters for example in the range between about 50 µm and about 100 µm. The particles can be administered alone or in any appropriate pharmaceutically acceptable vehicle, such as a liquid, for example saline, or a powder, for administration to the respiratory system.

Particles including a medicament, for example one or more of the drugs listed above, are administered to the respiratory tract of a patient in need of treatment, prophylaxis or diagnosis. Administration of particles to the respiratory system can be by means such as known in the art. For example, particles are delivered from an inhalation device. In a preferred embodiment, particles are administered via a dry powder inhaler (DPI). Metered-dose-inhalers (MDI) or instillation techniques also can be employed.

Various suitable devices and methods of inhalation which can be used to administer particles to a patient's respiratory tract are known in the art. For example, suitable inhalers are described in U.S. Pat. No. 4,069,819, issued Aug. 5, 1976 to Valentini, et al, U.S. Pat. No. 4,995,385 issued Feb. 26, 1991 to Valentini, et al., and U.S. Pat. No. 5,997,848 issued Dec. 7, 1999 to Patton, et al. Other examples include, but are not limited to, the SPINHALER® (Fisons, Loughborough, U.K.), ROTAHALER® (Glaxo-Wellcome, Research Triangle Technology Park, N.C.), FLOWCAPS® (Hovione, Loures, Portugal), INHALATOR® (Boehringer-Ingelheim, Germany), and the AEROLIZER® (Novartis, Switzerland), the DISKHALER® (Glaxo-Wellcome, RTP, NC) and others, such as known to those skilled in the art. Preferably, the particles are administered as a dry powder via a dry powder inhaler.

Preferably, particles administered to the respiratory tract travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. In a preferred embodiment of the invention, most of the mass of particles deposits in the deep lung. In another embodiment of the invention, delivery is primarily to the central airways. Delivery to the upper airways can also be obtained.

In one embodiment of the invention, delivery to the pulmonary system of particles is in a single, breath-actuated step, as described in U.S. Patent Application, High Efficient Delivery of a Large Therapeutic Mass Aerosol, application Ser. No. 09/591,307, filed Jun. 9, 2000, which is incorporated herein by reference in its entirety. In another embodiment of the invention, at least 50% of the mass of the particles stored in the inhaler receptacle is delivered to a subject's respiratory system in a single, breath-activated step. In a further embodiment, at least 5 milligrams and preferably at least 10 milligrams of a medicament is delivered by administering, in a single breath, to a subject's respiratory tract particles enclosed in the receptacle. Amounts as high as 15, 20, 25, 30, 35, 40 and 50 milligrams can be delivered.

As used herein, the term "effective amount" means the amount needed to achieve the desired therapeutic or diagnostic effect or efficacy. The actual effective amounts of drug can vary according to the specific drug or combination thereof being utilized, the particular composition formulated, the mode of administration, and the age, weight, condition of the patient, and severity of the symptoms or condition being treated. Dosages for a particular patient can be determined by one of ordinary skill in the art using conventional considerations, (e.g. by means of an appropriate, conventional pharmacological protocol). For example, effective amounts of albuterol sulfate range from about 100 micrograms (μg) to about 10 milligrams (mg).

Aerosol dosage, formulations and delivery systems also may be selected for a particular therapeutic application, as described, for example, in Gonda, I. "Aerosols for delivery of therapeutic and diagnostic agents to the respiratory tract," in *Critical Reviews in Therapeutic Drug Carrier Systems*, 6:273-313, 1990; and in Moren, "Aerosol dosage forms and formulations," in: *Aerosols in Medicine. Principles, Diagnosis and Therapy*, Moren, et al., Eds, Esevier, Amsterdam, 1985.

Drug release rates can be described in terms of release constants. The first order release constant can be expressed using the following equations:

$$M_{(t)} = M_{(\infty)} * (1 - e^{-k*t}) \quad (1)$$

Where k is the first order release constant. $M_{(\infty)}$ is the total mass of drug in the drug delivery system, e.g. the dry powder, and $M_{(t)}$ is the amount of drug mass released from dry powders at time t.

Equation (1) may be expressed either in amount (i.e., mass) of drug released or concentration of drug released in a specified volume of release medium. For example, Equation (1) may be expressed as:

$$C_{(t)} - C_{(\infty)} * (1 - e^{-k*t}) \text{ or } Release_{(t)} = Release_{(\infty)} * (1 - e^{-k*t}) \quad (2)$$

Where k is the first order release constant. $C_{(\infty)}$ is the maximum theoretical concentration of drug in the release medium, and $C_{(t)}$ is the concentration of drug being released from dry powders to the release medium at time t.

Drug release rates in terms of first order release constant can be calculated using the following equations:

$$k = -\ln(M_{(\infty)} - M_{(t)})/M_{(\infty)}/t \quad (3)$$

The release constants presented in Table 4 employ Equation (2).

As used herein, the term "a" or "an" refers to one or more.

The term "nominal dose" as used herein, refers to the total mass of bioactive agent which is present in the mass of particles targeted for administration and represents the maximum amount of bioactive agent available for administration.

EXEMPLIFICATION

Materials

Humulin L and Humulin R (human zinc insulin suspensions, 100 U/mL) and Humulin U (100 U/ml) were all purchased from Eli Lilly and Co. (Indianapolis, Ind.). Recombinant human insulin was also purchased from Eli Lilly and Co. and was in solid form as crystals containing 1% Zn.

Mass Median Aerodynamic Diameter-MMAD (μm)

The mass median aerodynamic diameter was determined using an Aerosizer/Aerodisperser (Amherst Process Instrument, Amherst, Mass). Approximately 2 mg of powder formulation was introduced into the Aerodisperser and the aerodynamic size was determined by time of flight measurements.

Volume Median Geometric Diameter-VMGD (μm)

The volume median geometric diameter was measured using a RODOS dry powder disperser (Sympatec, Princeton, N.J.) in conjunction with a HELOS laser diffractometer (Sympatec). Powder was introduced into the RODOS inlet and aerosolized by shear forces generated by a compressed air stream regulated at 2 bar. The aerosol cloud was subsequently drawn into the measuring zone of the HELOS, where it scattered light from a laser beam and produced a Fraunhofer diffraction pattern used to infer the particle size distribution and determine the median value.

The volume median geometric diameter was also determined using a Coulter Multisizer II. Approximately 5-10 mg powder formulation was added to 50 mL isoton II solution until the coincidence of particles was between 5 and 8%.

Determination of Plasma Insulin Levels

Quantification of insulin in rat plasma was performed using a human insulin specific RIA kit (Linco Research, Inc., St. Charles, Mo., catalog #HI-14K). The assay shows less than 0.1% cross reactivity with rat insulin. The assay kit procedure was modified to accommodate the low plasma volumes obtained from rats, and had a sensitivity of approximately 5 µU/mL.

Preparation of Insulin Formulations

The powder formulations listed in Table 1, with the exception of control Formulation No. 5, were prepared as follows. The experimental details set out below are specific for Formulation 2.

9.25 L of pH 2.5, 1.0 mM citrate buffer was prepared by dissolving 1.94 g of sodium citrate (Spectrum Labs) in 9.25 L of water and adjusting to pH 2.5 with 1 N HCl. 6.6 g of leucine (available from Spectrum) was dissolved into the citrate buffer followed by dissolving 3.3 g of recombinant human insulin (Eli Lilly and Co.) in the citrate/leucine solution. 2.178 g of zinc chloride was dissolved in 73.76 mL of water, and sonicated to achieve a homogenous solution. The $ZnCl_2$ solution was then added to the insulin/citrate/leucine solution. 1.0 N sodium hydroxide (NaOH) was then used to quickly adjust the solution to pH 6.7, resulting in precipitation of the zinc complexed insulin. A solution of DPPC in ethanol was prepared by dissolving 19.80 g of DPPC (Avati Polar Lipids, Alabaster, Ala.) in 23 L of 95% ethanol. The suspension of zinc complexed insulin was then added to the DPPC/ethanol solution. The final total solute concentration was 1.025 g/L comprising 0.60 g/L DPPC, 0.20 g/L leucine, 0.010 g/L recombinant insulin, 0.066 g/L $ZnCl_2$, and 0.059 g/L sodium citrate. In some studies, the final solute concentration was adjusted to 3.0 g/L by reducing the water and 95% ethanol to one third of the volumes described above.

The suspension was then used to produce dry powders. A Nitro mobile model Spray Dryer (Niro, Inc., Columbus, Md.) was used. Compressed air with variable pressure (1 to 5 bar) ran a rotary atomizer (2,000 to 30,000 rpm) located above the dryer. Liquid feed with varying rate (20 to 66 mL/min) was pumped continuously by an electronic metering pump (LMI, Model #A151-192s) to the atomizer. Both the inlet and outlet temperatures were measured. The inlet temperature was controlled manually; it could be varied between 100° C. and 400° C. and was established at 100, 110, 150, 175 or 200° C., with a limit of control of 5° C. The outlet temperature was determined by the inlet temperature and such factors as the gas and liquid feed rates (it varied between 50° C. and 130° C.). A container was tightly attached to the cyclone for collecting the powder product.

Preparation of Control Formulation 60/30/10 DPPC/Insulin/Sodium Citrate

The DPPC/citrate/insulin (60/10/30) spray drying solution was prepared by dissolving 600 mg DPPC in 600 mL of ethanol, dissolving 100 mg of sodium citrate and 300 mg of insulin (Eli Lilly and Co.) in 400 mL of water and then mixing the two solutions to yield one liter of cosolvent with a total solute concentration of 1 g/L (w/v). Higher solute concentrations of 3 g/L (w/v) were prepared by dissolving three times more of each solute in the same volumes of ethanol and water.

TABLE 1

| Formulation No. | DPPC % | Leucine % | Metal Cation Salt % | Sodium Citrate % | Insulin % | Cation/ Insulin % (w/w) % |
|---|---|---|---|---|---|---|
| 1<br>5% INSULIN/Zn | 58.5 | 24.4 | 6.4 | 5.9 | 4.9 | 63% |
| 2<br>10% INSULIN/Zn | 58.5 | 19.5 | 6.4 | 5.9 | 9.8 | 31% |
| 3<br>20% INSULIN/Zn | 58.5 | 9.8 | 6.4 | 5.9 | 19.5 | 16% |
| 4<br>30% INSULIN/Zn | 48.8 | 9.8 | 6.4 | 5.9 | 29.3 | 10% |
| 5†<br>30% INSULIN | 60 | 0.0 | 0 | 10 | 30 | 0.5% |
| 6<br>20% INSULIN/Zn | 64.2 | 5.3 | 2.6 | 6.4 | 21.4 | 58% |
| 7<br>20% INSULIN/Zn | 63.6 | 5.3 | 3.7 | 6.4 | 21.2 | 8.4% |
| 8<br>5% INSULIN/Zn<br>(SAME AS FORMULATION 1) | 58.5 | 24.4 | 6.4 | 5.9 | 4.9 | 63% |
| 9<br>5% INSULIN/Zn | 49.2 | 20.5 | 20.5 | 4.9 | 4.1 | 238% |
| 10<br>20% INSULIN/Zn | 66 | 13 | 1.0 | | 20 | 2.4% |
| 11<br>20% INSULIN/Zn | 66 | 11 | 3.1 | | 20 | 7.4% |
| 12<br>20% INSULIN/Zn | 64 | 10 | 6.3 | | 20 | 15% |
| 13<br>20% INSULIN/Zn | 58 | 10 | 12.5 | | 20 | 30% |
| 14<br>10% INSULIN/Zn | 64 | 20 | 6.3 | | 10 | 30% |
| 15<br>20% INSULIN/Cu | 66 | 13 | 1.0 | | 20 | 2.4% |
| 16<br>20% INSULIN/Cu | 66 | 14 | 0.1 | | 20 | 0.24% |

TABLE 1-continued

| Formulation No. | DPPC % | Leucine % | Metal Cation Salt % | Sodium Citrate % | Insulin % | Cation/ Insulin % (w/w) % |
|---|---|---|---|---|---|---|
| 17 20% INSULIN/Mg | 66 | 13 | 0.7 | | 20 | 0.9% |
| 18 20% INSULIN/Mg | 63 | 10 | 7.3 | | 20 | 9% |
| 19 20% INSULIN/Ca | 66 | 13 | 0.8 | | 20 | 1.4% |
| 20 20% INSULIN/Ca | 62 | 10 | 8.5 | | 20 | 15% |

†Control Formulation
% Represents amount % of each component in final dry formulation.
The Cation/Insulin % (w/w) ratio can be determined as follows:
Determine % of metal cation present in final formulation.
Calculate ratio of % of metal cation/% of Insulin in final formulation.

The physical characteristics of certain formulations from Table 1 are shown in Table 2. The data were obtained using the particle size analysis technique described above.

TABLE 2

| FORMULATION NO. | MMAD (μm) | MMGD (μm) |
|---|---|---|
| 1 | 2.1 | 7.15 |
| 2 | 2.95 | 7.09 |
| 3 | 2.46 | 7.32 |
| 4 | 3.53 | 6.05 |
| 5 | 2.24 | 14

TABLE 3-continued

PLASMA INSULIN CONCENTRATION (μU/mL) ± S.E.M.

| Time (hrs.) | Humulin L | No. 1 | No. 2 | No. 3 | No. 4 | No. 5 |
|---|---|---|---|---|---|---|
| 8 | 5.5 ± 2.1 | 32.0 ± 13.3 | 33.6 ± 6.4 | 18.6 ± 5.6 | 4.5 ± 1.2 | 5.2 ± 0.1 |
| 12 | N.S. | 9.3 ± 2.7 | 8.0 ± 1.9 | 10.7 ± 3.1 | 3.8 ± 0.4 | N.S. |
| 24 | N.S. | 4.2 ± 0.6 | 4.4 ± 0.4 | 4.4 ± 0.4 | 3.6 ± 0.2 | N.S. |
| n | 8 | 4 | 4 | 4 | 4 | 6 |

N.S. = Not Sampled

In Vitro Analysis of Insulin-Containing Formulations

The in vitro release of insulin containing dry powder formulations was performed as described by Gietz et al. in *Eur. J. Pharm. Biopharm.*, 45:259-264 (1998), with several modifications. Briefly, in 20 mL screw-capped glass scintillation vials about 10 mg of each dry powder formulation was mixed with 4 mL of warm (37° C.) 1% agarose solution using polystyrene stir bars. The resulting mixture was then distributed in 1 mL aliquots to a set of five fresh 20 mL glass scintillation vials. The dispersion of dry powder in agarose was cooled in an ambient temperature dessicator box protected from light to allow gelling. Release studies were conducted on an orbital shaker at about 37° C. At predetermined time points, previous release medium (1.5 mL) was removed and fresh release medium (1.5 mL) was added to each vial. Typical time points for these studies were 5 minutes, 1, 2, 4, 6 and 24 hours. The release medium used consisted of 20 mM 4-(2-hydroxyethyl)-piperazine-1-ethanesulfonic acid (HEPES), 138 mM NaCl, 0.5% Pluronic (Synperonic PE/F68; to prevent insulin filbrillation in the release medium); pH 7.4. A Pierce (Rockford, Ill.) protein assay kit (See *Anal Biochem*, 150:76-85 (1985)) using known concentrations of insulin standard was used to monitor insulin concentrations in the release medium.

Table 4 summarizes the in vitro release data and first order release constants for powder formulations of Table 1 comprising insulin Humulin R, L and U.

TABLE 4

| Formulation No. | Cumulative % Insulin Released at 6 hours | Cumulative % Insulin Released at 24 hours | First Order Release Constants (hr$^{-1}$) |
|---|---|---|---|
| Humulin R | 92.67 ± 0.36 | 94.88 ± 0.22 | 1.0105 ± 0.2602 |
| Humulin L | 19.43 ± 0.41 | 29.71 ± 0.28 | 0.0924 ± 0.0183 |
| Humulin U | 5.71 ± 0.18 | 12.65 ± 0.43 | 0.0158 ± 0.0127 |
| 1 | 5.30 ± 0.79 | 6.90 ± 2.43 | 0.2577 ± 0.0463 |
| 4 | 15.70 ± 2.59 | 21.60 ± 2.44 | 0.2793 ± 0.0410 |
| 5 (Fast Release) | 78.47 ± 0.40 | 85.75 ± 0.63 | 0.5232 ± 0.0861 |
| 2 | 5.30 ± 0.28 | 20.09 ± 0.41 | 0.0248 ± 0.0055 |
| 10 | 2.69 ± 1.24 | 21.12 ± 0.90 | 0.0015 ± 0.0453 |
| 11 | 4.46 ± 1.32 | 15.04 ± 4.54 | 0.0251 ± 0.0170 |
| 13 | 2.82 ± 0.10 | 3.85 ± 0.10 | 0.2360 ± 0.2325 |
| 12 | 1.80 ± 0.22 | 4.29 ± 1.56 | 0.0698 ± 0.0169 |
| 14 | 6.24 ± 0.15 | 11.17 ± 0.30 | 0.1281 ± 0.0352 |
| 19 | 31.69 ± 3.42 | 74.32 ± 0.23 | 0.0741 ± 0.0629 |
| 20 | 46.66 ± 3.09 | 71.79 ± 0.75 | 0.1709 ± 0.0192 |
| 17 | 58.13 ± 1.88 | 81.49 ± 0.95 | 0.2109 ± 0.0787 |
| 18 | 58.19 ± 1.74 | 81.92 ± 0.82 | 0.2064 ± 0.0425 |
| 16 | 45.37 ± 1.74 | 103.08 ± 0.58 | 0.0797 ± 0.0655 |
| 15 | 72.86 ± 0.93 | 101.88 ± 1.36 | 0.2139 ± 0.1035 |

$Release_{(t)} = Release_{(\infty)} * (1 - e^{-k*t})$

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of delivery to the pulmonary system comprising:
    administering to the respiratory tract of a patient in need of treatment, prophylaxis or diagnosis an effective amount of a dry powder comprising:
    a) a multivalent metal cation which is complexed with a therapeutic, prophylactic or diagnostic agent;
    b) a pharmaceutically acceptable carrier; and
    c) a multivalent metal cation-containing component wherein the dry powder is spray-dried and has a total amount of multivalent metal cation which is about 10% w/w or more of the total weight of the agent, a tap density of about 0.4 g/cm³ or less, a median geometric diameter of between about 5 micrometers and about 30 micrometers and an aerodynamic diameter of from about 1 to about 5 microns.

2. The method of claim 1, wherein the biologically active agent is a protein.

3. The method of claim 2, wherein the protein is insulin.

4. The method of claim 2, wherein the multivalent metal cation is selected from Zn(II), Ca(II), Cu(II), Ni(II), Co(II), Fe(II), Ag(II), Mn(II), Mg(II) or Cd(II).

5. The method of claim 4, wherein the multivalent metal cation is Zn(II).

6. The method of claim 2, wherein the multivalent metal cation is present at about 3% w/w or more of the total weight of the agent.

7. The method of claim 2, wherein the multivalent metal cation is present at about 50% w/w or more of the total weight of the agent.

8. The method of claim 2, wherein complexation of the agent and multivalent metal cation comprises a metal coordination.

9. The method of claim 2, wherein the dry powder has a tap density about 0.1 g/cm³ or less.

10. The method of claim 2, wherein the dry powder has an aerodynamic diameter of from about 1 to about 3 microns.

11. The method of claim 2, wherein the dry powder has an aerodynamic diameter of from about 3 to about 5 microns.

12. The method of claim 2, wherein delivery to the pulmonary system includes delivery to the deep lung.

13. The method of claim 2, wherein delivery to the pulmonary system includes delivery to the central airways.

14. The method of claim 2, wherein delivery to the pulmonary system includes delivery to the upper airways.

15. The method of claim 2, wherein the dry powder further comprise a carboxylic acid.

16. The method of claim 15, wherein the carboxylic acid includes at least two carboxyl groups.

17. The method of claim 16, wherein the carboxylic acid is citric acid or a salt thereof.

18. The method of claim 2, wherein the dry powder further comprise an amino acid.

19. The method of claim 18, wherein the amino acid is hydrophobic.

20. The method of claim 19, wherein the hydrophobic amino acid is leucine, isoleucine, alanine, valine, phenylalanine or any combination thereof.

21. The method of claim 2 wherein the pharmaceutically acceptable carrier is a phospholipid.

22. The method of claim 21 wherein the phospholipid is a phosphatidic acid, a phosphatidylcholine, a phosphatidylalkanolamine, a phosphatidylethanolamine, a phosphatidylglycerol, a phosphatidylserine, a phosphatidylinositol or combinations thereof.

23. A method of delivery to the pulmonary system comprising:
   administering to the respiratory tract of a patient in need of treatment, prophylaxis or diagnosis an effective amount of a dry powder comprising:
   a) a protein which is complexed with zinc;
   b) a pharmaceutically acceptable carrier; and
   c) a multivalent metal cation-containing component wherein the dry powder is spray-dried and has a total amount of multivalent metal cation which is about 10% w/w or more of the total weight of the agent, a tap density of about 0.4 g/cm$^3$ or less, a median geometric diameter of between about 5 micrometers and about 30 micrometers and an aerodynamic diameter of from about 1 to about 5 microns.

24. The method of claim 23, wherein the dry powder has a tap density about 0.1 g/cm$^3$ or less.

25. The method of claim 23, wherein the pharmaceutically acceptable carrier is a phospholipid.

26. The method of claim 23 wherein the dry powder further comprises a carboxylic acid.

27. A composition for delivery to the pulmonary system comprising:
   administering to the respiratory tract of a patient in need of treatment, prophylaxis or diagnosis an effective amount of a dry powder comprising:
   a) a protein which is complexed with zinc;
   b) a pharmaceutically acceptable carrier; and
   c) a multivalent metal cation-containing component wherein the dry powder is spray-dried and has a total amount of multivalent metal cation which is about 10% w/w or more of the total weight of the agent, a tap density of about 0.4 g/cm$^3$ or less, a median geometric diameter of between about 5 micrometers and about 30 micrometers and an aerodynamic diameter of from about 1 to about 5 microns.

28. The method of claim 27, wherein the dry powder has a tap density about 0.1 g/cm$^3$ or less.

29. The method of claim 27, wherein the pharmaceutically acceptable carrier is a phospholipid.

30. The method of claim 27 wherein the dry powder further comprises a carboxylic acid.

\* \* \* \* \*

UNITED STATES PATENT AND TRADEMARK OFFICE
CERTIFICATE OF CORRECTION

PATENT NO. : 7,678,364 B2  Page 1 of 1
APPLICATION NO. : 09/822716
DATED : March 16, 2010
INVENTOR(S) : David A. Edwards and Jeffery S. Hrkach It is certified that error appears in the above-identified patent and that said Letters Patent is hereby corrected as shown below:

Claim 6, Column 22, line 44, after "about" delete "3%" and replace with --30%--.

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,678,364 B2 | Page 1 of 1 |
| APPLICATION NO. | : 09/822716 | |
| DATED | : March 16, 2010 | |
| INVENTOR(S) | : David A. Edwards et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,800 days.

Signed and Sealed this

Seventh Day of December, 2010

David J. Kappos
*Director of the United States Patent and Trademark Office*